(12) United States Patent
Sun et al.

(10) Patent No.: US 10,548,883 B2
(45) Date of Patent: Feb. 4, 2020

(54) BENZOTRIAZOLE-DERIVED α AND β-UNSATURATED AMIDE COMPOUND USED AS TGF-β RI INHIBITOR

(71) Applicants: GENFLEET THERAPEUTICS (SHANGHAI) INC., Shanghai (CN); MEDSHINE DISCOVERY INC., Nanjing, Jiangsu (CN)

(72) Inventors: Fei Sun, Shanghai (CN); Lifang Wu, Shanghai (CN); Charles Z. Ding, Shanghai (CN); Guoping Hu, Shanghai (CN); Jian Li, Shanghai (CN); Shuhui Chen, Shanghai (CN); Jianyu Lu, Shanghai (CN)

(73) Assignees: Genfleet Therapeutics (Shanghai) Inc., Shanghai (CN); Medshine Discovery Inc., Nanjing (CN)

( * ) Notice: Subject to any disclaimer, the term of this patent is extended or adjusted under 35 U.S.C. 154(b) by 0 days.

(21) Appl. No.: 16/308,859

(22) PCT Filed: Jun. 8, 2017

(86) PCT No.: PCT/CN2017/087546
§ 371 (c)(1),
(2) Date: Dec. 11, 2018

(87) PCT Pub. No.: WO2017/215506
PCT Pub. Date: Dec. 21, 2017

(65) Prior Publication Data
US 2019/0151299 A1 May 23, 2019

(30) Foreign Application Priority Data
Jun. 13, 2016 (CN) .......................... 2016 1 0410554

(51) Int. Cl.
*A61K 31/4439* (2006.01)
*A61P 35/00* (2006.01)
*C07D 471/04* (2006.01)

(52) U.S. Cl.
CPC .......... *A61K 31/4439* (2013.01); *A61P 35/00* (2018.01); *C07D 471/04* (2013.01)

(58) Field of Classification Search
None
See application file for complete search history.

(56) References Cited

FOREIGN PATENT DOCUMENTS

| CN | 1511157 A | 7/2004 |
| CN | 1681501 A | 10/2005 |
| CN | 103025731 A | 4/2013 |
| WO | 02094833 A1 | 11/2002 |
| WO | 2004026306 A2 | 4/2004 |
| WO | 2004050659 A1 | 6/2004 |
| WO | 2004072033 A2 | 8/2004 |
| WO | 2007076127 A2 | 7/2007 |
| WO | 2009009059 A1 | 1/2009 |
| WO | 2012002680 A2 | 1/2012 |

OTHER PUBLICATIONS

International Search Report of PCT/CN2017/087546 dated Sep. 5, 2017.
Written Opinion of PCT/CN2017/087546 dated Sep. 5, 2017.
Berge et al., "Pharmaceutical Salts", Journal of Pharmaceutical Science 66: 1-19 (1977).
Maehr, "A proposed new convention for graphic presentation of molecular geometry and topography", J. Chem. Ed. 1985, 62: 114-120.
Remington,The Science and Practice of Pharmacy, 21st Ed., Lippincott, Williams & Wilkins (2005).

*Primary Examiner* — Alicia L Otton
(74) *Attorney, Agent, or Firm* — Harness, Dickey & Pierce, P.L.C.

(57) ABSTRACT

A benzotriazole-derived α and β-unsaturated amide compound used as TGF-βR1 inhibitor or a pharmaceutically acceptable salt thereof, the structure of the compound being as shown in formula (I).

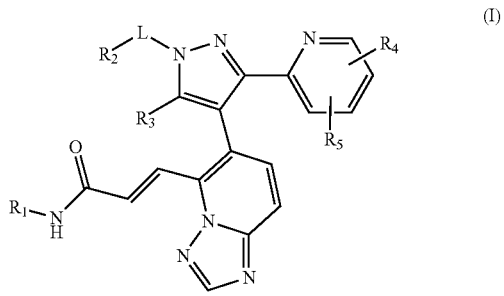

19 Claims, 2 Drawing Sheets

BENZOTRIAZOLE-DERIVED α AND β-UNSATURATED AMIDE COMPOUND USED AS TGF-β RI INHIBITOR

CROSS REFERENCE TO RELATED APPLICATIONS

This application is a U.S. National Phase Application under 35 U.S.C. 371 of International Application No. PCT/CN/2017/087546 filed on Jun. 8, 2017. This application claims priority to Chinese Application No. 201610410554.8, filed on Jun. 13, 2016. The entire disclosures of all of the above application are incorporated herein by reference.

FIELD OF INVENTION

The present invention relates to a benzotriazole-derived α and β-unsaturated amide compound used as TGF-βRI inhibitor, and particularly relates to a compound represented by formula (I) or a pharmaceutically acceptable salt thereof.

PRIOR ARTS

Transforming growth factor beta (TGF-β) is a multifunctional cytokine belonging to the transforming growth factor superfamily with a broad range of biological activities involved in early embryonic development, cartilage and bone formation, extracellular matrix synthesis, inflammation, interstitial fibrosis, regulation of immune and endocrine functions, tumor formation and development.

The TGF-β superfamily consists of a class of polypeptide growth factors whose structure and function are correlated, including TGF-βs (i.e. narrowly-defined TGF-β), activins, inhibins, and bone morphogenetic proteins (BMPs) namely Mullerian, etc., and TGF-β is one of the important members of this family. In mammals, TGF-β mainly exists in three forms of TGF-β1, TGF-β2 and TGF-β3, which are located on different chromosomes. Among them, TGF-β1 accounts for the highest proportion (>90%) in somatic cells, and it is the most active, the most versatile, and most widely distributed one. The newly synthesized TGF-β appears as an inactive precursor, consisting of a signal peptide, a latent-associated polypeptide (LAP) and a mature TGF-β. After enzymatic hydrolysis, it forms active TGF-β, and then binds to receptor to exert biological effects.

Signals are transduced by TGF-β signal molecules through a transmembrane receptor complex. TGF-β receptor is a transmembrane protein present on the cell surface and is divided into type I receptor (TGF-βRI), type II receptor (TGF-βRII) and type III receptor (TGF-βRIII), of which TGF-βRI is also known as activin receptor-like kinase 5 (ALK5). TGF-βRIII lacks intrinsic activity, and the lack is mainly related to the storage of TGF-β. TGF-βRI and TGF-βRII belong to the serine/threonine kinase family. Type II receptors bind to TGF-β ligands with higher affinity and form heterologous receptor complexes with type I receptors. Phosphorylation of a glycine- and serine-rich region (GS domain) in the proximal membrane of type I receptors initiates intracellular signal-cascade reactions.

Smads is an important TGF-β signal transduction and regulation molecule in cells which can directly transfer TGF-β signal into the nucleus from the cell membrane. Thus, TGF-β/Smads signaling pathway plays an important role in the occurrence and development of tumors. In TGF-β/Smads signal transduction, activated TGF-β firstly binds to TGF-βRII on the cell membrane surface to form a heterodimeric complex, and TGF-βRI recognizes and binds to the binary complex.

TGF-βRII phosphorylates serine/threonine in the GS domain of the cytoplasmic domain of TGF-βRI to activate TGF-βRI. Then activated TGF-βRI further phosphorylates R-Smads (Smad2/Smad3) protein, and the latter binds to Co-Smad (Smad4) to form a heterotrimeric complex which enters the nucleus and acts synergistically with other co-activators and co-inhibitors to regulate transcription of target genes. Any change in the TGF-beta/Smads signaling pathway can lead to abnormalities in the signal transduction pathway.

Current research indicates that in tumor cells, TGF-β can directly affect tumor growth (non-intrinsic effects of TGF-β signal), or indirectly affects tumor growth (intrinsic effects of TGF-β) by inducing epithelial-mesenchymal transformation, blocking anti-tumor immune responses, increasing tumor-associated fibrosis and enhanced angiogenesis. At the same time, TGF-β has a strong fibrotic induction, which is an activator of tumor-associated fibroblasts. These fibroblasts are a major source of collagen type I and other fibrotic factors. Induction products of fibroblasts and other fibrotic factors may continue to develop a microenvironment which can reduce immune responses, increases drug resistance, and potentiates tumor angiogenesis. In addition, TGF-β affects angiogenesis during both ontogenesis and tumor growth. For example, TGF-βRI-deficient mouse embryos show severe vascular development defects, demonstrating that the TGF-β signaling pathway is a key regulator in vascular endothelium and smooth muscle cell development.

In 2013, the FDA awarded Lilly's small molecule TGF-βRI inhibitor LY2157299 (WO 2002/094833) for the treatment of glioma and liver cancer. LY2157299 is an orphan drug understudied, named Galunisertib. Galunisertib inhibits tumor cell invasion and metastasis while inhibiting the infiltration of tumor cells into blood vessels. In the phase 2 clinical trial of patients with liver cancer, about 23% of patients treated with Galunisertib had a decrease in serum alpha-fetoprotein (AFP) level of more than 20%. These patients had slower tumor progression and longer survival than those without AFP response, and increased expression of cadherin in epithelial cells was also observed in these patients, suggesting that Galunisertib can regulate EMT by inhibiting the TGF-β signaling pathway, thereby inhibiting the progression of liver cancer.

The structure of Galunisertib (LY2157299) is shown as formula (II):

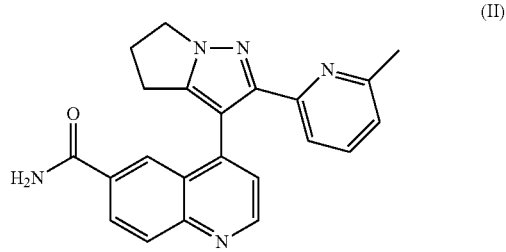 [SMILES: Cc1cccc(-c2nn3c(c2-c2ccnc4ccc(C(N)=O)cc24)CCC3)n1]

References of background:
WO 2009/009059; WO 2007/076127; WO 2004/026306; WO 2004/072033; WO 2002/094833.

CONTENT OF THE PRESENT INVENTION

The present invention provides a compound represented by formula (I) or a pharmaceutically acceptable salt thereof,

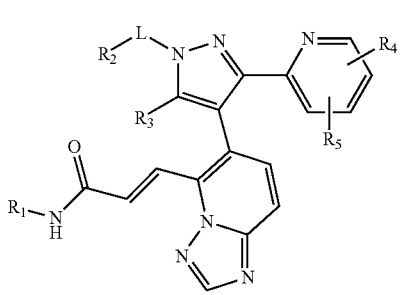

(I)

wherein,

R₁ is selected from hydrogen, hydroxyl, amino, or from the group consisting of $C_{1-3}$ alkyl, and $C_{3-6}$ cycloalkyl, and the group is optionally substituted by 1, 2, or 3 R(s);

R₂ is selected from the group consisting of $C_{1-3}$ alkyl, $C_{3-6}$ cycloalkyl and phenyl, and the group is optionally substituted by 1, 2, or 3 R(s);

R₃ is selected from hydrogen, or from $C_{1-3}$ alkyl which is optionally substituted by 1, 2, or 3 R(s);

optionally, R₂ and R₃ link together to form a 5-6 membered ring, which is optionally substituted by 1, 2, or 3 R(s);

each of R₄ and R₅ is independently selected from hydrogen, halogen, or selected from the group consisting of $C_{1-3}$ alkyl and $C_{1-3}$ heteroalkyl, and the group is optionally substituted by 1, 2, or 3 R(s);

L is selected from a single bond, —(CRR)$_{1-3}$—;

R is selected from F, Cl, Br, I, CN, OH, NH₂, COOH, or from the group consisting of $C_{1-6}$ alkyl, $C_{1-6}$ heteroalkyl, $C_{3-6}$ cycloalkyl, 3-6 membered heterocycloalkyl, phenyl and 5-6 membered heteroaryl, and the group is optionally substituted by 1, 2, or 3 R'(s);

R' is selected from F, Cl, Br, I, OH, CN, NH₂, COOH, Me, Et, CF₃, CHF₂, CH₂F, NHCH₃, N(CH₃)₂;

"hetero" refers to a heteroatom or a heteroatomic group selected from the group consisting of —C(=O)N(R)—, —N(R)—, —C(=NR)—, —S(=O)₂N(R)—, —S(=O)N(R)—, —O—, —S—, =O, =S, —O—N=, —C(=O)O—, —C(=O)—, —C(=S)—, —S(=O)—, —S(=O)₂—, —N(R)C(=O)N(R)—;

in any of the above cases, the number of the heteroatom or the heteroatomic group is independently selected from 1, 2, or 3.

In some embodiments of the present invention, R is selected from F, Cl, Br, I, CN, OH, or from the group consisting of $C_{1-6}$ alkyl, $C_{3-6}$ cycloalkyl and phenyl, and the group is optionally substituted by 1, 2, or 3 R'(s).

In some embodiments of the present invention, R is selected from the group consisting of F, Cl, Br, I, CN, OH, methyl, CHF₂, ethyl, propyl, cyclopropyl and phenyl.

In some embodiments of the present invention, R₁ is selected from hydrogen, or from the group consisting of methyl, ethyl,

and the group is optionally substituted by 1, 2, or 3 R(s).

In some embodiments of the present invention, R₁ is selected from hydrogen, methyl, ethyl,

In some embodiments of the present invention, R₂ is selected from the group consisting of methyl, ethyl, isopropyl, cyclopentyl and phenyl, and the group is optionally substituted by 1, 2, or 3 R(s).

In some embodiments of the present invention, R₂ is selected from the group consisting of methyl, ethyl, isopropyl, cyclopentyl

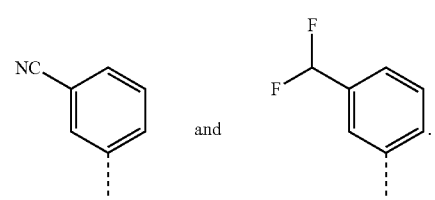

In some embodiments of the present invention, R₂ and R₃ link together, and the moiety

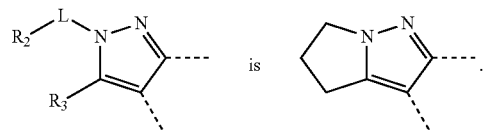

In some embodiments of the present invention, each of R₄ and R₅ is independently selected from the group consisting of hydrogen, F, Cl, Br, methyl and ethyl.

In some embodiments of the present invention, the moiety

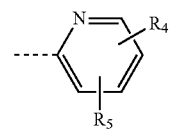

is selected from

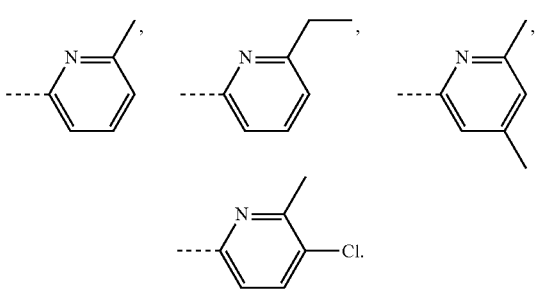

In some embodiments of the present invention, L is selected from a single bond, —(CH₂)$_{1-3}$—.

In some embodiments of the present invention, L is selected from a single bond, —CH₂—, —CH₂CH₂—.

In some embodiments of the present invention, R is selected from F, Cl, Br, I, CN, OH, or from the group consisting of $C_{1-6}$ alkyl, $C_{3-6}$ cycloalkyl and phenyl, and the group is optionally substituted by 1, 2, or 3 R'(s), and other variables are defined as above.

In some embodiments of the present invention, R is selected from F, Cl, Br, I, CN, OH, methyl, CHF$_2$, ethyl, propyl, cyclopropyl and phenyl, and other variables are defined as above.

In some embodiments of the present invention, R$_1$ is selected from hydrogen, or from the group consisting of methyl, ethyl,

and the group is optionally substituted by 1, 2, or 3 R(s), and other variables are defined as above.

In some embodiments of the present invention, R$_1$ is selected from hydrogen, methyl, ethyl,

and other variables are defined as above.

In some embodiments of the present invention, R$_2$ is selected from the group consisting of methyl, ethyl, isopropyl, cyclopentyl and phenyl, and the group is optionally substituted by 1, 2, or 3 R(s), and other variables are defined as above.

In some embodiments of the present invention, R$_2$ is selected from the group consisting of methyl, ethyl, isopropyl, cyclopentyl

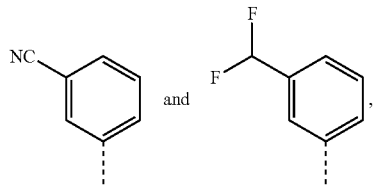

and other variables are defined as above.

In some embodiments of the present invention, R$_2$ and R$_3$ link together, and the moiety

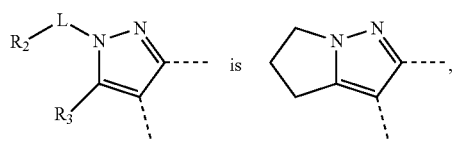

and other variables are defined as above.

In some embodiments of the present invention, each of R$_4$ and R$_5$ is independently selected from the group consisting of hydrogen, F, Cl, Br, methyl and ethyl, and other variables are defined as above.

In some embodiments of the present invention, the moiety

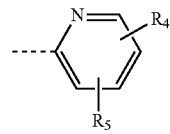

is selected from

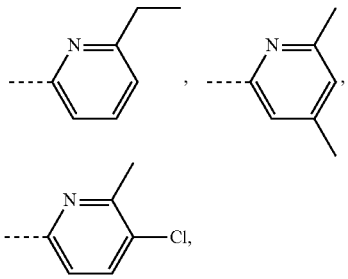

and other variables are defined as above.

In some embodiments of the present invention, L is selected from a single bond, —(CH$_2$)$_{1-3}$—, and other variables are defined as above.

In some embodiments of the present invention, L is selected from a single bond, —CH$_2$—, —CH$_2$CH$_2$—, and other variables are defined as above.

In some embodiments of the present invention, the compound is selected from

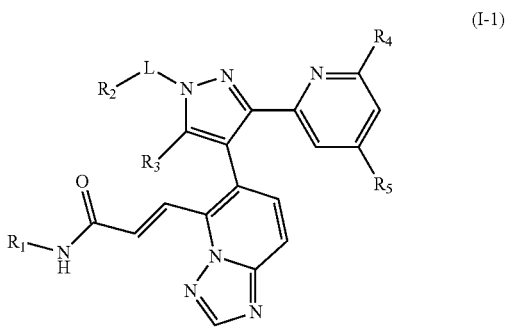

(I-1)

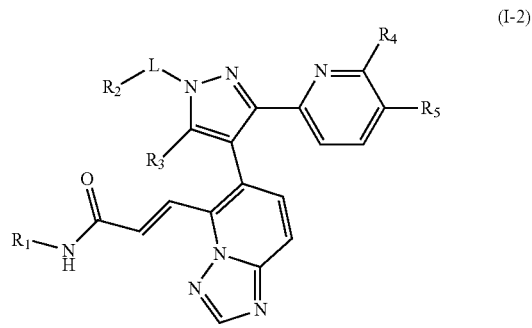

(I-2)

wherein, R$_1$, R$_2$, R$_3$, R$_4$, R$_5$, and L are defined as above, and R$_4$ and R$_5$ are not both hydrogen simultaneously.

In some embodiments of the present invention, the compound is selected from

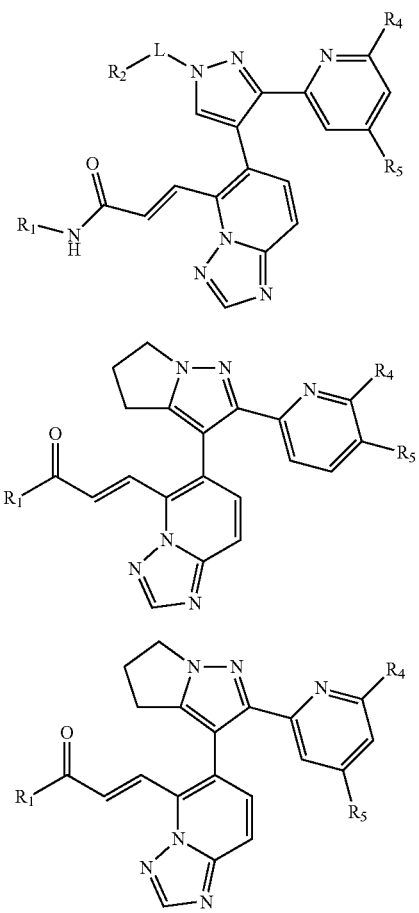
(I-a)
(I-b)
(I-c)
wherein, $R_1$, $R_2$, $R_4$, $R_5$, and L are defined as above, and $R_4$ and $R_5$ are not both hydrogen simultaneously.
The present invention also provides a compound or a pharmaceutically acceptable salt thereof, which is selected from the group consisting of
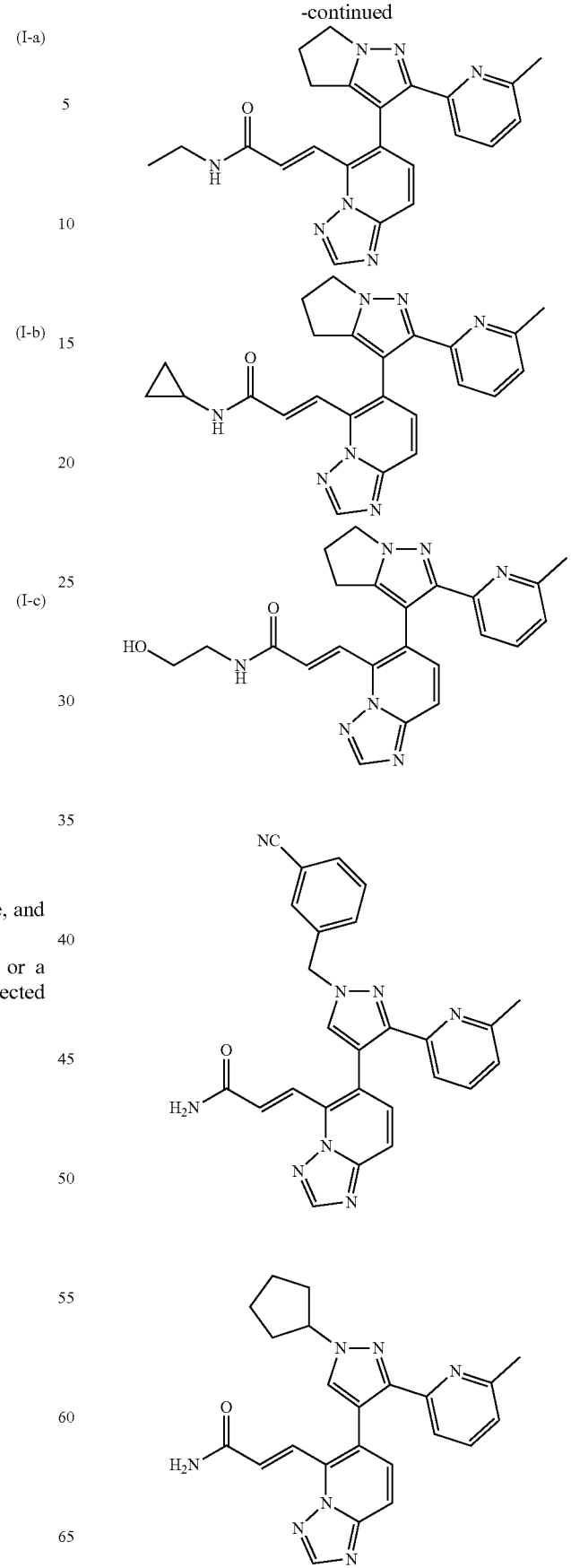

-continued

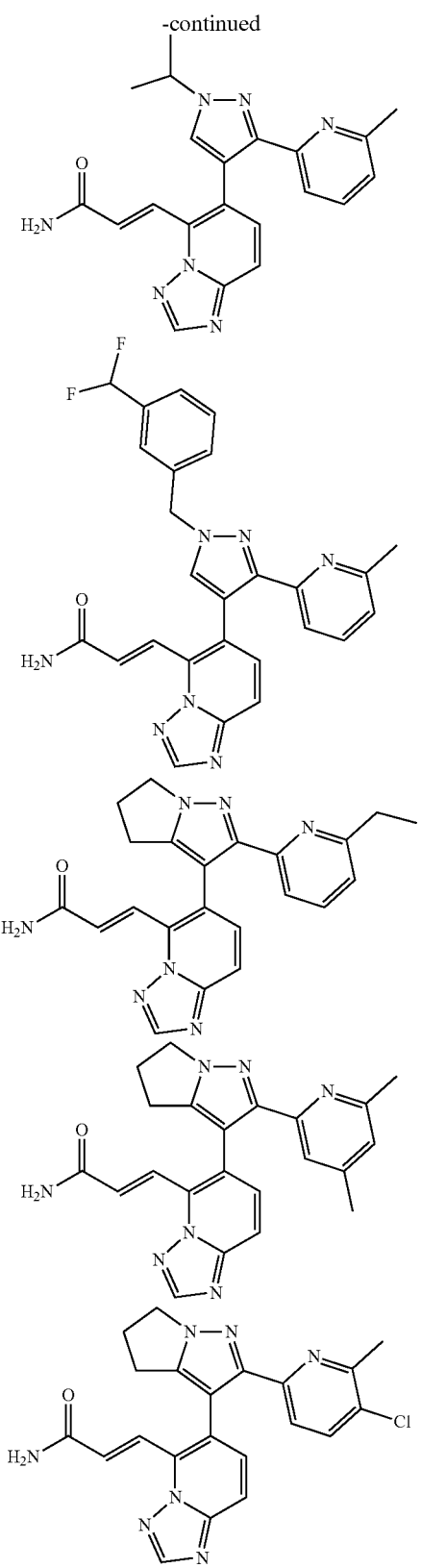

The present invention also provides a pharmaceutical composition comprising a therapeutically effective dose of the compound or the pharmaceutically acceptable salt thereof, and a pharmaceutically acceptable carrier.

The present invention also provides a use of the compound or the pharmaceutically acceptable salt thereof or the pharmaceutical composition in manufacturing a medicament for the treatment of cancer.

In some embodiments of the present invention, the cancer refers to breast cancer.

Other embodiments of the present invention are derived from the random combination of the above variables.

TECHNICAL EFFECT

The use of the compound of the present invention is mainly as an inhibitor of TGF-beta R1, which blocks the downstream signaling pathway of TGF-betade by inhibiting TGF-beta R1, thereby exerting a desired pharmacological action. Unlike the prior art, the benzotriazole structure of the compound of the present invention is an important pharmacophore that binds to TGF-beat R1. Unexpectedly, the combination of the chemical structures of the compounds of the present invention results in superior biological activity over the prior art. At the same dose, in the CT-26 Syngeneic model of mice, the tumor suppressing effect of the compound of the present invention used alone and in combination with PDL-1 were both superior to the prior art, revealing that the compound of the present invention has superior anti-tumor immune activation; in the mouse 4T1 orthotopic transplantation anti-metastatic breast cancer model, the compound of the present invention have significantly superior anti-metastatic ability compared to the prior art. The compound of the present invention has obvious inhibitory effect on the metastasis and metastasis intensity of tumor on multi-tissue organs, indicating its great potential as a therapeutic drug. The compound of the present invention is very promising as a metastasis inhibitor of breast cancer, and plays an important role in metastasis inhibition in the combined treatment of breast cancer, and provides a potential new therapeutic strategy for the treatment of clinical breast cancer.

DEFINITION AND DESCRIPTION

Unless otherwise specified, the following terms and phrases used herein are intended to have the following meanings. A particular term or phrase should not be considered indefinite or unclear when not specifically defined, but should be understood in the ordinary sense. When a trade name appears in this document, it is intended to refer to its corresponding article or the active ingredient thereof. The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salts" refers to salts of the compounds of the present invention that are prepared from the compounds having particular substituents of the present invention and relatively non-toxic acids or bases. When the compounds of the present invention contain relatively acidic functional groups, base addition salts can be obtained by contacting the neutrality form of such compounds with a sufficient amount of a base in pure solution or in a suitable inert solvent. Pharmaceutically acceptable base addition salts include salts of sodium, potassium, calcium, ammonium, organic ammonia or magnesium or similar salts. When compounds of the present invention contain relatively basic functional groups, acid addition salts can be obtained by contacting the neutrality form of such compounds with a sufficient amount of the acid in pure solution or in a suitable inert solvent. Examples of pharmaceutically acceptable acid addition salts include inorganic acid salts including, for example, hydrochloric acid, hydrobromic acid, nitric acid, carbonic acid, bicarbonate, phosphoric acid, monohydrogen phosphate, dihydrogen phosphate, sulfuric acid, bisulfate, hydroiodic acid, phosphorous acid and the like; and organic acid salts including, for example, acetic acid, propionic acid, isobutyric acid, maleic acid, malonic acid, benzoic acid, succinic acid, suberic acid, fumaric acid, lactic acid, mandelic acid, phthalic acid, benzene sulfonic acid, p-toluene sulfonic acid, citric acid, tartaric acid, methanylulfonic acid and the like; also includes salts of amino acids (e.g., arginine, etc.) as well as salts of organic acids such as glucuronic acid (see Berge et al., "Pharmaceutical Salts", Journal of Pharmaceutical Science 66: 1-19 (1977)). Certain specific compounds of the present invention contain basic and acidic functional groups so that they can be converted to any base or acid addition salt.

Preferably, the salt is contacted with a base or acid in a conventional manner and the parent compound is isolated, thereby regenerating the neutrality form of the compound. The parent form of a compound differs from its various salt forms in certain physical properties, such as solubility in polar solvents.

As used herein, "pharmaceutically acceptable salts" belong to derivatives of the compounds of the present invention, wherein the parent compound is modified by salt formation with an acid or by salt formation with a base. Examples of pharmaceutically acceptable salts include, but are not limited to: inorganic or organic acid salts of base radicals such as amines, inorganic or organic salts of acid radicals such as carboxylic acids, and the like. Pharmaceutically acceptable salts include the conventional non-toxic salts or quaternary ammonium salts of the parent compound, such as the salts formed by non-toxic inorganic or organic acids. The conventional non-toxic salts include, but are not limited to, salts derived from inorganic and organic acids which are selected from the group consisting of 2-acetoxybenzoic acid, 2-hydroxyethylsulfonic acid, acetic acid, ascorbic acid, benzosulfonic acid, benzoic acid, bicarbonate, carbonic acid, citric acid, edetic acid, ethanedisulfonic acid, ethanesulfonic acid, fumaric acid, glucoheptonose, gluconic acid, glutamic acid, glycolic acid, hydrobromic acid, hydrochloric acid, hydroiodide, hydroxy, hydroxynaphthyl, isethionic acid, lactic acid, lactose, dodecyl sulfonic acid, maleic acid, malic acid, mandelic acid, methane sulfonic acid, nitric acid, oxalic acid, pamoic acid, pantothenic acid, phenylacetic acid, phosphoric acid, polygalactanaldehyde, propionic acid, salicylic acid, stearic acid, acetic acid, succinic acid, sulfamic acid, sulfanilic acid, sulfuric acid, tannins, tartaric acid and p-toluenesulfonic acid.

The pharmaceutically acceptable salts of the present invention can be synthesized from the parent compound containing acid radicals or base radicals by conventional chemical methods. In general, such salts are prepared by the reaction of these compounds in free acid or base form with a stoichiometric amount of the appropriate base or acid in water or an organic solvent or a mixture of the two. In general, non-aqueous media such as ether, ethyl acetate, ethanol, isopropanol or acetonitrile are preferred.

In addition to salt forms, the compounds provided herein also exist in prodrug forms. The prodrugs of the compounds described herein are readily chemically altered under physiological conditions to be converted into the compounds of the invention. In addition, prodrugs can be converted to the compounds of the present invention by chemical or biochemical methods in the in vivo environment.

Certain compounds of the present invention may exist in unsolvated or solvated forms, including hydrated forms. In general, solvated forms are equivalent to unsolvated forms and both are included within the scope of the present invention.

Certain compounds of the present invention may have asymmetric carbon atoms (optical centers) or double bonds. Racemates, diastereomers, geometric isomers and individual isomers are all included within the scope of the present invention.

The graphical representation of racemic, ambiscalemic and scalemic or enantiomeric pure compounds herein is from Maehr, J. Chem. Ed. 1985, 62: 114-120. Unless otherwise specified, the absolute configuration of a stereocenter is represented by a wedge bond and a dashed bond. When the compounds described herein contain olefinic double bonds or other geometric asymmetry centers, they include E, Z geometric isomers, unless otherwise specified. Likewise, all tautomeric forms are included within the scope of the present invention.

The compounds of the invention may exist in specific geometric or stereoisomeric forms. The present invention encompasses all such compounds, including cis and trans isomers, (−)- and (−)-pair enantiomers, (R)- and (S)-enantiomers, diastereoisomers, (D)-isomer, (L)-isomer, and the racemic mixtures and other mixtures thereof, such as enantiomeric or diastereomeric enriched mixtures, all of which are within the scope of the present invention. Additional asymmetric carbon atoms may be present in the substituents such as alkyl groups. All these isomers and their mixtures are included within the scope of the present invention.

Optically active (R)- and (S)-isomers and D and L isomers can be prepared by chiral synthesis or chiral reagents or other conventional techniques. If an enantiomer of a certain compound of the invention is desired, it can be prepared by asymmetric synthesis or derivatization with a chiral auxiliary, wherein the resulting mixture of diastereomers is separated and the ancillary groups are cleaved to provide pure desired enantiomer. Alternatively, when the molecule contains a basic functional group (such as an amino group) or an acidic functional group (such as a carboxyl group), a diastereomer salt is formed with a suitable optically active acid or base, and then the diastereomeric resolution is performed by conventional methods known in the art, and then the pure enantiomer is recovered. In addition, the separation of enantiomers and diastereomers is generally accomplished by the use of chromatography using a chiral stationary phase and optionally in combination with chemical derivatization (e.g., forming carbaminate from amines).

The compounds of the present invention may contain unnatural proportions of atomic isotopes at one or more of the atoms that comprise the compound. For example, the compounds can be labelled with radioactive isotopes such as tritium ($^3$H), iodine-125 ($^{125}$I) or C-14 ($^{14}$C). The variants of all isotopic compositions of the compounds of the present invention, whether radioactive or not, are all included within the scope of the present invention.

The term "pharmaceutically acceptable carrier" refers to any agent or carrier medium capable of delivering an effective amount of an active agent of the present invention without interfering with the biological activity of the active agent and having no toxic side effects on the host or patient. Exemplary carriers include water, oil, vegetables and minerals, cream bases, lotion bases, ointment bases, etc. These bases include suspending agents, tackifiers, transdermal enhancers and the like. Their formulations are well known to those skilled in the cosmetic area or topical medicine area. For additional information on carriers, reference may be made to *Remington: The Science and Practice of Pharmacy*, 21st Ed., Lippincott, Williams & Wilkins (2005), the contents of which are incorporated herein by reference.

The term "excipient" generally refers to the carrier, diluent, and/or medium required to formulate an effective pharmaceutical composition.

For a drug or pharmacologically active agent, the term "effective amount" or "therapeutically effective amount" refers to a sufficient amount of drug or agent that is nontoxic but can achieve the desired effect. For an oral dosage form in the present invention, an "effective amount" of an active substance in the composition refers to the amount needed to achieve the desired effect when used in combination with another active substance in the composition. The determination of the effective amount varies from person to person, depending on the age and general condition of the recipient, and also on the specific active substance, and the appropriate effective amount in an individual case can be determined by a person skilled in the art according to routine experimentation.

The terms "active ingredient", "therapeutic agent", "active substance" or "active agent" refers to a chemical entity that can effectively treat a target disorder, disease or condition.

"Optional" or "optionally" means that an event or situation described subsequently may, but not necessarily, occur, and the description includes the occurrence of the event or situation mentioned above and the absence of the event or situation described therein.

The term "substituted" means that any one or more hydrogen atoms on a particular atom are replaced with substituents, including deuterium and hydrogen variants, as long as the valence of a particular atom is normal and the substituted compound is stable. When the substituent is a keto (i.e., =O), it means that two hydrogen atoms are substituted. Ketone substitution does not occur on aromatic groups. The term "optionally substituted" means that it may or may not be substituted. Unless otherwise specified, the type and number of substituents may be arbitrary on the basis of being chemically achievable.

When any variant (e.g., R) occurs more than once in the composition or structure of a compound, its definition in each case is independent. Thus, for example, if a group is substituted by 0-2 R, the group may optionally be substituted with up to two R, and R in each case has an independent option. In addition, combinations of substituents and/or variants thereof are permissible only if such combinations result in stable compounds.

When the number of a linking group is 0, such as —(CRR)$_0$—, it means that the linking group is a single bond.

When one of the variants is selected from a single bond, it means that the two groups which it connects are directly linked. For example, when L represents a single bond in A-L-Z, the structure is actually A-Z.

When a substituent is vacant, it means that the substituent does not exist. For example, when X is vacant in A-X, it means that the structure is actually A. When a substituent's bond can be cross-linked to two atoms on a ring, the substituent can be bonded to any atom on the ring. When the recited substituents do not indicate by which atom they are attached to a compound included in the general formula of the chemical structure but are not specifically mentioned, such substituents may be bonded through any of their atoms. Combinations of substituents and/or variants thereof are permissible only if such combinations result in stable compounds. For example, a structure unit

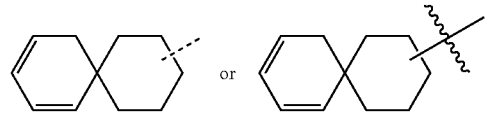

signifies that it may be substituted at any position on the cyclohexyl or cyclohexadiene.

Unless otherwise specified, the term "hetero" denotes a heteroatom or a heteroatom group (i.e., an atom group containing heteroatoms), including atoms other than carbon (C) and hydrogen (H), and atom groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)—, or —S(=O)N(H)—.

Unless otherwise specified, "ring" refers to a substituted or unsubstituted cycloalkyl, heterocycloalkyl, cycloalkenyl, heterocycloalkenyl, cycloalkynyl, heterocycloalkynyl, aryl, or heteroaryl. The so-called ring includes a single ring, a bicyclic ring, a spiro ring, a ring system having two rings sharing one bond, or a bridged ring. The number of atoms on the ring is usually defined as the number of members of the ring. For example, a "5-7 membered ring" refers to that 5 to 7 atoms are arranged in a circle. Unless otherwise specified, the ring optionally contains 1 to 3 heteroatoms. Thus, a "5-7 membered ring" includes, for example, phenyl, pyridinyl, and piperidinyl; in another aspect, the term "5-7 membered heterocycloalkyl ring" includes pyridyl and piperidinyl, but does not include phenyl. The term "ring" also includes ring systems containing at least one ring, wherein, each "ring" independently meets the above definition.

Unless otherwise specified, the term "heterocycle" or "heterocyclyl" means stable monocyclic, bicyclic, or tricyclic rings containing heteroatoms or heteroatom groups, which may be saturated, partially unsaturated, or unsaturated (aromatic), and contain carbon atoms and 1, 2, 3, or 4 heterocyclic atoms independently selected from N, O and S, wherein any of the above heterocycles may be fused to a benzene ring to form a bicyclic ring. The nitrogen and sulfur heteroatoms can be optionally oxidized (i.e. NO and S(O)p, p is 1 or 2). The nitrogen atom may be substituted or unsubstituted (i.e. N or NR, where R is H or other substituents as already defined herein). The heterocycles may be attached to the pendant groups of any heteroatom or carbon atom to form a stable structure. If the resulting compound is stable, the heterocycles described herein may be substituted at the carbon or nitrogen position. The nitrogen atom in the heterocycle is optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed 1. As used herein, the term "aromatic heterocyclic group" or "heteroaryl" means a stable 5, 6 or 7 membered monocyclic or bicyclic or 7, 8, 9 or 10 membered bicyclic heterocyclyl aromatic ring, which contains carbon atoms and 1, 2, 3, or 4 heterocyclic atoms independently selected from N, O, and S. The nitrogen atom may be substituted or unsubstituted (i.e., N or NR, where R is H or other substituents as already defined herein). The nitrogen and sulfur heteroatoms can be optionally oxidized (i.e., NO and S(O)p, p is 1 or 2). It is worth noting that the total number of S and O atoms on the aromatic heterocycle does not exceed 1. Bridged rings are also included in the definition of heterocycles. A bridged ring is formed when two non-adjacent carbon or nitrogen atoms are connected by one or more atoms (i.e., C, O, N or S). A preferred bridged ring includes, but is not limited to, one carbon atom, two carbon atoms, one nitrogen atom, two nitrogen atoms, and one carbon-nitrogen group. It is worth noting that a bridge always converts a single ring into a three ring. In the bridged ring, substituents on the ring can also appear on the bridge.

Examples of heterocyclic compounds include, but are not limited to, acridinyl, azocinyl, benzimidazolyl, benzofuranyl, benzosulfydrylfuranyl, benzosulfydrylphenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyldecahydroquinolinyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indolyl, indolylalkenyl, indolinyl, indolizinyl, indonyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazinyl, phenothiazinyl, benzoxanthinyl, phenoxazinyl, phenazinyl, piperazinyl, piperidinyl, piperidinone, 4-piperidinone, piperonyl, pteridyl, purinyl, pyranyl pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthienyl, thiazolyl, isothiazolylthiophenyl, thienooxazolyl, thienothiazolyl, thienoimidazolyl, thienyl, triazinyl, 1,2,3-triazolyl, 1,2,4-triazolyl, 1,2,5-triazolyl, 1,3,4-triazolyl, and xanthene. Also included are fused-ring and spiro compounds.

Unless otherwise specified, the term "hydrocarbyl" or its subordinate concept (such as alkyl, alkenyl, alkynyl, phenyl, and the like) by itself or as part of another substituent means linear, branched, or cyclic hydrocarbon radicals, or combinations thereof, which may be fully saturated (such as alkyl), unitary or polyunsaturated (such as alkenyl, alkynyl, phenyl), may be mono-substituted, di-substituted, or poly-substituted, and may be monovalent (such as methyl), divalent (such as methylene), or polyvalent (such as methine), may include divalent or polyvalent radicals, and have a specified number of carbon atoms (e.g., $C_1$-$C_{12}$ represents 1 to 12 carbons, $C_1$-$C_{12}$ are selected from the group of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ selected from the group of $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic and aromatic hydrocarbyl, wherein the aliphatic hydrocarbyl includes chain and cyclic structures, including but not limited to alkyl, alkenyl, alkynyl, and the aromatic hydrocarbyl includes but not limited to 6-12 membered aromatic hydrocarbyl such as benzene, naphthalene, and the like. In some embodiments, the term "hydrocarbyl" refers to linear or branched chain radicals or combinations thereof, which may be fully saturated, unitary or polyunsaturated, and may include divalent and polyvalent radicals. Examples of saturated hydrocarbon radicals include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and homologues or isomers of n-pentyl, n-hexyl, n-heptyl, n-octyl and other atom groups. Unsaturated alkyl has one or more double or triple bonds, examples of which include, but are not limited to, vinyl, 2-propenyl, butenyl, crotyl, 2-prenyl, 2-(butadienyl), 2,4-pentadienyl, 3-(1,4-pentadienyl), ethynyl, 1- and 3-propynyl, 3-butynyl, and more advanced homologues or isomers.

Unless otherwise specified, the term "heterohydrocarbyl" or its subordinate concept (such as heteroalkyl, heteroalkenyl, heteroalkynyl, heteroaryl, etc.) by itself or in combination with another term means stable, linear, branched or cyclic hydrocarbon radicals or combinations thereof, consisting of a certain number of carbon atoms and at least one heteroatom. In some embodiments, the term "heteroalkyl" by itself or in combination with another term means stable, linear, branched hydrocarbon radicals or combinations thereof, consisting of a certain number of carbon atoms and at least one heteroatom. In a typical embodiment, the heteroatom is selected from the group consisting of B, O, N, and S, wherein the nitrogen and sulfur atoms are optionally oxidized and the nitrogen heteroatoms are optionally quaternized. The heteroatom or heteroatom group may be located at any internal position of the heterohydrocarbyl (including the position where the hydrocarbyl is attached to the rest of the molecule). Examples include but are not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two heteroatoms may be continuous, such as —$CH_2$—NH—$OCH_3$.

Unless otherwise specified, the terms "cyclohydrocarbyl", "heterocyclohydrocarbyl" or subordinate concepts (such as aryl, heteroaryl, cycloalkyl, heterocycloalkyl, cycloalkenyl, heterocycloalkenyl, cycloalkynyl, heterocycloalkynyl, etc.) by itself or in combination with other terms mean cyclized "hydrocarbyl", "heterohydrocarbyl" respectively. In addition, for heterohydrocarbyl or heterocyclohydrocarbyl (such as heteroalkyl, heterocycloalkyl), heteroatoms may occupy the position at which the heterocycle is attached to the rest of the molecule. Examples of include, but are not limited to, cyclopentyl, cyclohexyl, 1-cyclohexenyl, 3-cyclohexenyl, cycloheptyl and the like. Non-limiting examples of heterocyclic groups include 1-(1,2,5,6-tetrahydropyridinyl), 1-piperidinyl, 2-piperidinyl, 3-piperidinyl, 4-morpholinyl, 3-morpholinyl, tetrahydrofuran-2-yl, tetrahydrofuranindol-3-yl, tetrahydrothiophen-2-yl, tetrahydrothiophen-3-yl, 1-piperazinyl, and 2-piperazinyl.

Unless otherwise specified, the terms "alkyl" means linear or branched saturated hydrocarbyl, which may be mono-substituted or poly-substituted, and may be monovalent (such as methyl), divalent (such as methylene), or polyvalent (such as methine). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl), etc.

Unless otherwise specified, the terms "alkenyl" means an alkyl having one or more carbon-carbon double bonds at any position of the chain, which may be mono-substituted or poly-substituted, and may be monovalent, divalent, or polyvalent. Examples of alkenyl include vinyl, propenyl, butenyl, pentenyl, hexenyl, butadienyl, piperylene, hexadienyl, etc.

Unless otherwise specified, the term "alkynyl" means an alkyl having one or more carbon-carbon triple bonds at any position of the chain, which may be mono-substituted or poly-substituted, and may be monovalent, divalent, or polyvalent. Examples of alkynyl include ethynyl, propynyl, butynyl, pentynyl, etc.

Unless otherwise specified, the cycloalkyl includes any stable cyclic or polycyclic hydrocarbon group, and any carbon atom is saturated, which may be mono-substituted or poly-substituted, and may be monovalent, divalent, or polyvalent. Examples of cycloalkyl include, but are not limited to, cyclopropyl, norbornyl, [2.2.2]bicyclooctane, [4.4.0]bicyclononane, etc.

Unless otherwise specified, the cycloalkenyl includes any stable cyclic or polycyclic hydrocarbon group containing one or more unsaturated carbon-carbon double bonds at any position of the ring, which may be mono-substituted or poly-substituted, and may be monovalent, divalent, or polyvalent. Examples of cycloalkenyl include, but are not limited to, cyclopentenyl, cyclohexenyl, etc.

Unless otherwise specified, the cycloalkynyl includes any stable cyclic or polycyclic hydrocarbon group containing one or more unsaturated carbon-carbon triple bonds at any position of the ring, which may be mono-substituted or poly-substituted, and may be monovalent, divalent, or polyvalent.

Unless otherwise specified, the term "halo" or "halogen" by itself or as part of another substituent denotes a fluorine, chlorine, bromine, or iodine atom. In addition, the term "haloalkyl" is meant to include monohaloalkyl and polyhaloalkyl. For example, the term "halo($C_1$-$C_4$)alkyl" is meant to include but not limited to trifluoromethyl, 2,2,2-trifluoroethyl, 4-chlorobutyl, 3-bromopropyl, and the like. Unless otherwise specified, examples of haloalkyl include, but are not limited to, trifluoromethyl, trichloromethyl, pentafluoroethyl, and pentachloroethyl.

"Alkoxy" represents the above alkyl having a specified number of carbon atoms attached through an oxygen bridge, and unless otherwise specified, $C_{1-6}$ alkoxy includes alkoxy of $C_1$, $C_2$, $C_3$, $C_4$, $C_5$ and $C_6$. Examples of alkoxy include, but are not limited to, methoxy, ethoxy, n-propoxy, isopropoxy, n-butoxy, sec-butoxy, tert-butoxy, n-pentyloxy and S-pentyloxy. Unless otherwise specified, the term "aryl" refers to a polyunsaturated aromatic hydrocarbon substituent, which may be mono-substituted or poly-substituted, and may be monovalent, divalent, or polyvalent, and may be monocyclic or polycyclic rings (such as 1 to 3 rings; at least one of which is aromatic), being fused together or covalently linked. The term "heteroaryl" refers to an aryl group (or ring) containing one to four heteroatoms. In one illustrative example, the heteroatom is selected from the group consisting of B, N, O, and S, wherein the nitrogen and sulfur atoms are optionally oxidized and the nitrogen atom is optionally quaternized. A heteroaryl can be attached to the rest of the molecule through a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-iso quinolinyl, 5-isoquinolinyl, 2-quinoxalinyl, 5-quinoxalinyl, 3-quinolinyl, and 6-quinolinyl. The substituents for any of the above aryl and heteroaryl ring systems are selected from the acceptable substituents described below.

Unless otherwise specified, aryl groups, when used in combination with other terms (e.g., aryloxy, arylthio, arylalkyl) include aryl and heteroaryl rings as defined above. Thus, the term "aralkyl" is intended to include those groups (e.g., benzyl, phenethyl, pyridylmethyl, etc.) where the aryl group is attached to the alkyl group, and including those alkyl groups where the carbon atom (e.g., methylene) has been substituted by an atom such as oxygen, for example, phenoxymethyl, 2-pyridyloxymethyl 3-(1-naphthyloxy)propyl and the like.

The term "leaving group" refers to a functional group or atom that can be substituted by another functional group or atom through a substitution reaction (e.g., an affinity substitution reaction). For example, representative leaving groups include triflate; chlorine, bromine, iodine; sulfonate groups such as mesylate, tosylate, p-bromobenzenesulfonate, p-toluenesulfonates and the like; acyloxy such as acetoxy, trifluoroacetoxy and the like.

The term "protecting group" includes but is not limited to "amino protecting group", "hydroxy protecting group" or "sulfhydryl protecting group". The term "amino protecting group" refers to a protecting group suitable for blocking a side reaction at the amino nitrogen position. Representative amino protecting groups include, but are not limited to, formyl; acyl, such as alkanoyl (e.g., acetyl, trichloroacetyl, or trifluoroacetyl); alkoxycarbonyl, such as tert-butoxycarbonyl (Boc); arylmethoxycarbonyl such as benzyloxycarbonyl (Cbz) and 9-fluorenylmethyloxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group that is suitable for blocking the side reaction of hydroxyl groups. Representative hydroxy protecting groups include, but are not limited to, alkyl such as methyl, ethyl, and tert-butyl; acyl such as alkanoyl (such as acetyl); arylmethyl such as benzyl (Bn), p-methoxybenzyl (PMB), 9-fluorenylmethyl (Fm) and diphenylmethyl (benzhydryl, DPM); silyl such as trimethylsilyl (TMS) and tert-butyl dimethylsilyl (TBS) and the like.

The compounds of the present invention may be prepared by a variety of synthetic methods well-known to those skilled in the art, including the embodiments set forth below, combinations thereof with other chemical synthesis methods, and equivalent alternatives well-known to those skilled in the art, preferred embodiments include but are not limited to embodiments of the present invention.

The solvents used in the present invention are commercially available.

The present invention uses the following abbreviations: aq for water; HATU for O-(7-azabenzotriazol-1-yl)-N,N,N', N'-tetramethyluronium hexafluorophosphate; EDC for N-(3-dimethylaminopropyl)-N'-ethylcarbodiimide hydrochloride; m-CPBA for 3-chloroperoxybenzoic acid; eq for equivalent, equal; CDI for carbonyldiimidazole; DCM for dichloromethane; PE for petroleum ether; DIAD for diisopropyl azodicarboxylate; DMF for N,N-dimethylformamide; DMSO for dimethyl sulfoxide; EtOAc for ethyl acetate ester; EtOH for ethanol; McOH for methanol; CBz for benzyloxycarbonyl, an amine protecting group; BOC for tert-butoxycarbonyl, an amine protecting group; HOAc for acetic acid; $NaCNBH_3$ for sodium cyanoborohydride; r.t. for room temperature; O/N for overnight; THF for tetrahydrofuran; $Boc_2O$ for di-tert-butyl dicarbonate; TFA for trifluoroacetic acid; DIPEA for diisopropylethylamine; SOCl$_2$ for thionyl chloride; CS$_2$ for carbon disulfide; TsOH for p-toluenesulfonic acid; NFSI for N-fluoro-N-(phenylsulfonyl)phenylsulfonyl amide; NCS for 1-chloropyrrolidine-2,5-dione; n-Bu$_4$NF for tetrabutylammonium fluoride; iPrOH for 2-propanol; mp for melting point; LDA for lithium diisopropylamide, FBS for fetal bovine serum; DPBS for Dulbecco's phosphate buffered saline; EDTA for ethylenediaminetetraacetic acid; DMEM for Dulbecco's modified eagle medium; CellTiter-Glo (CTG) for ATP fluorescence activity detection method; PO for gastrointestinal administration; IP for intraperitoneal administration.

Compounds are named by hand or ChemDraw® software, and commercially available compounds are named after supplier catalog names.

DETAILED DESCRIPTION OF THE PREFERRED EMBODIMENT

Figure 1:
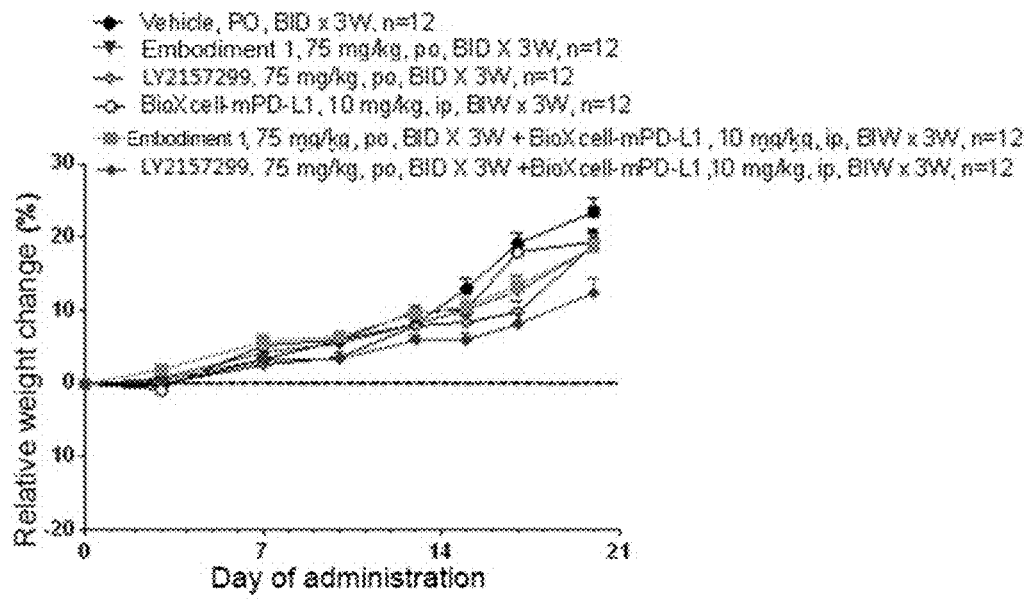
FIG. 1 is the effect of Embodiment 1, LY2157299 and BioXcell-mPD-L1 on the body weight of female BALB/c mouse model of CT-26 cell subcutaneous xenograft tumor.

The following examples further illustrate the present invention, but the present invention is not limited thereto. While the present invention has been described in detail and with reference to specific embodiments thereof, it will be apparent to those skilled in the art that various changes and modifications can be made therein without departing from the spirit and scope thereof.

Embodiment 1

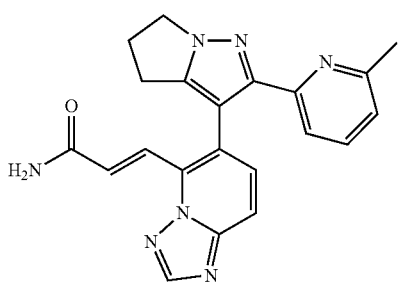 [SMILES: Cc1cccc(-c2nn3c(c2-c2ccc4ncnn4c2/C=C/C(N)=O)CCC3)n1]

Preparation of Intermediate 1-6

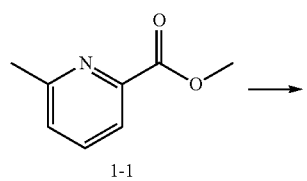

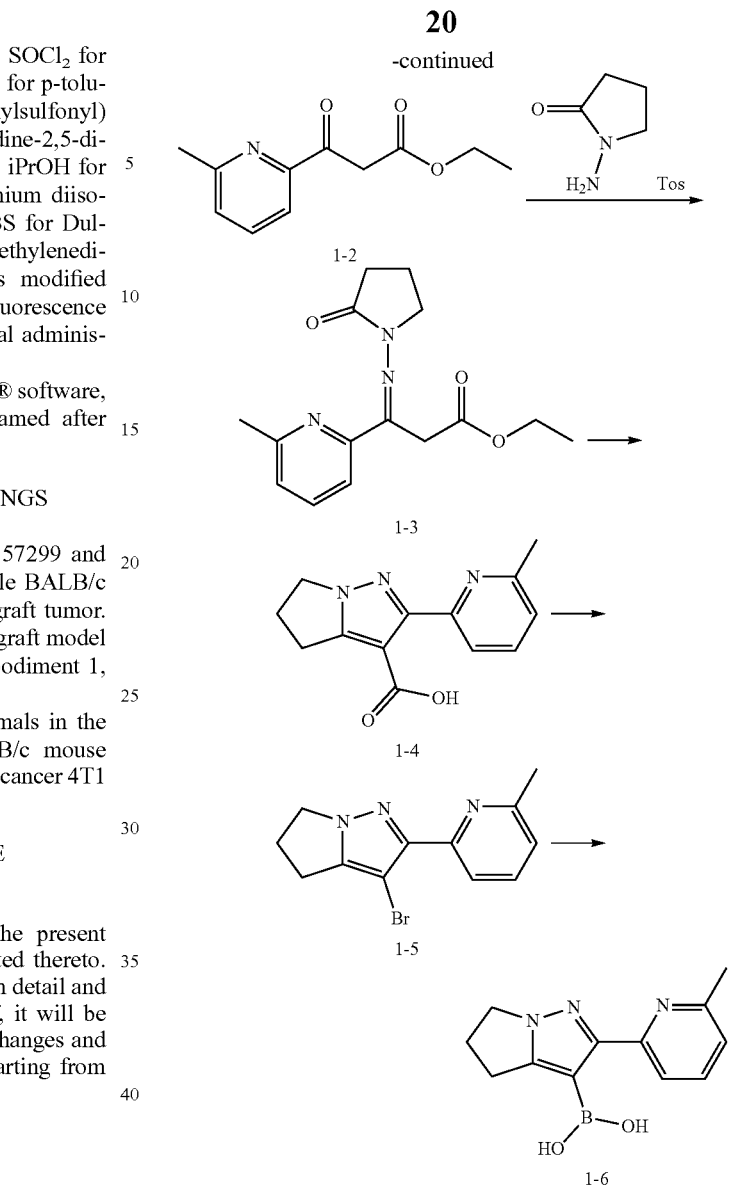

Step A: Ethyl acetate (291.41 mL, 2.98 mol) was dissolved in toluene (750.00 mL), and then sodium ethoxide (135.06 g, 1.98 mol) was added in batches at room temperature, and the mixture was stirred at room temperature for 1 h. Methyl 6-methylpyridine-2-carboxylate (150.00 g, 992.33 mmol) was added to the above reaction solution at 25° C., then heated to 95° C. and stirred for 15 h. The reaction mixture was cooled to 30° C., adjusted to pH 7 with acetic acid, diluted with water (500 mL), and extracted with ethyl acetate (500 mL). The organic phase was dried over anhydrous sodium sulfate, filtered and concentrated under reduced pressure. The residue was purified by silica gel chromatograph (eluent: petroleum ether/ethyl acetate=50/1) to give ethyl 3-(6-methylpyridin-2-yl)-3-oxopropanoate (120.00 g, yield: 58.35%).

Step B: ethyl 3-(6-methylpyridin-2-yl)-3-oxopropanoate (120.00 g, 579.07 mmol) was dissolved in pyridine (300 mL), and then 1-aminopyrrolidin-2-one p-toluenesulfonate (172.01 g, 631.66 mmol) was added. The reaction mixture was stirred at 25° C. for 16 h and then concentrated under reduced pressure to remove solvent. The residue was diluted with water (300 mL) and then extracted with ethyl acetate (300 mL*2). The combined organic phases were dried over anhydrous sodium sulfate, filtered and concentrated under reduced pressure to give ethyl 3-(6-methylpyridin-2-yl)-3-(2-oxopyrrolidin-1-yl)imino)propanoate (150 g, yield: 90.28%).

Step C: ethyl 3-(6-methylpyridin-2-yl)-3-((2-oxopyrrolidin-1-yl)imino)propanoate (155.00 g, 535.72 mmol) was dissolved in toluene, then sodium ethoxide (72.91 g, 1.07 mol) was added. The reaction mixture was heated to 100° C. and stirred for 16 h, then cooled to room temperature. It was slowly diluted with water (1.5 L), adjusted to pH 4 with concentrated hydrochloric acid, and extracted with dichloromethane/isopropyl alcohol (10/1) (1 L×7). The combined organic layers were dried over anhydrous sodium sulfate, filtered and concentrated under reduced pressure. The residue was triturated with petroleum ether/ethyl acetate=10/1 (200 mL), filtered and the solid was collected. Then the solid was dried under reduced pressure to give 2-(6-methylpyridin-2-yl)-5,6-dihydro-4H-pyrrolo[1,2-b]pyrazole-3-carboxylic acid (52.80 g, yield: 40.52%).

Step D: 2-(6-methylpyridin-2-yl)-5,6-dihydro-4H-pyrrolo[1,2-b]pyrazole-3-carboxylic acid (45.00 g, 184.99 mmol) was dissolved in N,N-dimethylformamide (650.00 mL), and then NBS (49.09 g, 258.99 mmol) was added. The reaction mixture was stirred at 30-40° C. for 60 h, then diluted with water (600 mL) and extracted with dichloromethane/isopropyl alcohol (10/1) (500 mL×3). The combined organic phases were washed once with sodium hydroxide (0.5 mol/L, 800 mL), dried over anhydrous sodium sulfate, filtered and concentrated under reduced pressure. Then the resulting solid was triturated with petroleum ether/ethyl acetate=10/1 (200 mL), filtered and the solid was collected. The solid was dried under reduced pressure to give 3-bromo-2-(6-methylpyridin-2-yl)-5,6-dihydro-4H-pyrrolo[1,2-b]pyrazole (33.00 g, yield: 64.13%).

Step E: 3-bromo-2-(6-methylpyridin-2-yl)-5,6-dihydro-4H-pyrrolo[1,2-b]pyrazole (1.00 g, 3.60 mmol) and triisopropyl borate (1.79 g, 9.54 mmol) were dissolved in tetrahydrofuran (20.00 mL). The reaction mixture was cooled to minus 70° C., then n-butyllithium (2.5 M, 3.74 mL) was added dropwise. After completion of the dropwise addition, the reaction mixture was stirred at 25° C. for 1 h, and then the pH was adjusted to 7 with aqueous hydrochloric acid (0.5 mol/L), and then concentrated under reduced pressure to remove tetrahydrofuran and cooled to 15° C. The mixture was filtered, and the filter cake was triturated with petroleum ether/ethyl acetate=10/1 (200 mL), filtered and the solid was collected. The solid was dried under reduced pressure to give (2-(6-methylpyridin-2-yl)-5,6-dihydro-4H-pyrrolo[1,2-b]pyrazol-3-yl)boronic acid (750 mg, yield: 85.71%).

Preparation of Embodiment 1

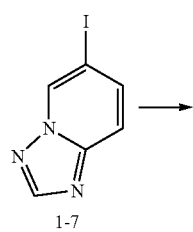

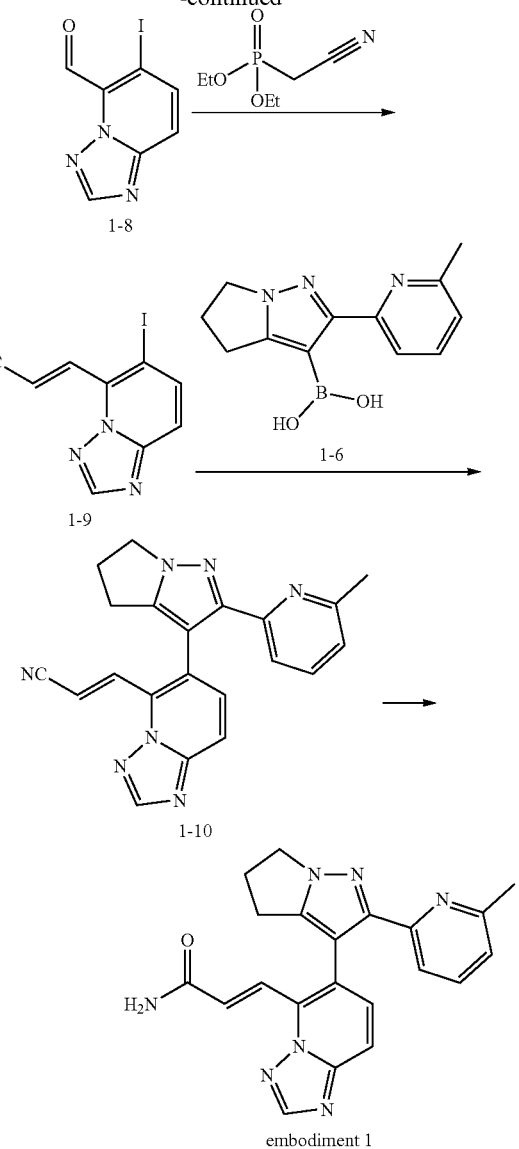

Step A: 6-iodo-[1,2,4]triazolo[1,5-a]pyridine (16.00 g, 65.30 mmol) was dissolved in tetrahydrofuran (800.00 mL) and cooled to −60-−70° C., and then lithium hexamethyldisilazide (1 mol/L, 130.60 mL, 65.30 mmol) was added dropwise. The reaction mixture was stirred at −60-−70° C. for 15 min and N,N-dimethylformamide (14.32 g, 195.90 mmol, 15.07 mL) was added. The reaction mixture was further stirred at −60-−70° C. for 15 min and then quenched with saturated aqueous ammonium chloride (500 mL). The reaction mixture was warmed to room temperature and then extracted with ethyl acetate (500 mL×2). The combined organic layers were washed with brine (500 mL), dried over anhydrous sodium sulfate, filtered and concentrated under reduced pressure. The residue was purified by silica gel chromatograph (eluent: dichloromethane/ethyl acetate=10/1) to afford 6-iodo-[1,2,4]triazolo[1,5-a]pyridine-5-carbaldehyde (6.40 g, yield: 35.90%). $^1$H NMR (400 MHz, DMSO-d6) δ 10.46 (s, 1H), 8.62 (s, 1H), 8.16 (d, J=9.3 Hz, 1H), 7.88 (d, J=9.3 Hz, 1H).

Step B: 2-diethoxyphosphorylacetonitrile (3.83 g, 21.61 mmol, 3.48 mL) and tetrahydrofuran (80 mL) were added into a 500 mL three-necked flask equipped with a thermometer and a nitrogen balloon. The mixture was cooled to 0° C. And then potassium t-butoxide (2.42 g, 21.61 mmol) was added in batches. The reaction mixture was stirred at 0° C. for 15 min and then added dropwise to another suspension through a dropping funnel (6-iodo-[1,2,4]triazolo[1,5-a]pyridine-5-carbaldehyde dispersed in tetrahydrofuran (120 mL) and cooled to 0° C.). The reaction mixture was stirred at 0° C. for 15 min then quenched with water (300 mL), extracted with ethyl acetate (200 mL) and dichloromethane (200 mL). The combined organic phase was washed with brine (300 mL), dried over anhydrous sodium sulfate, filtered and concentrated under reduced pressure. The residue was purified by silica gel chromatograph (eluent: dichloromethane/ethyl acetate=200/1 to 10/1) to give (E)-3-(6-iodo-[1,2,4]triazolo[1,5-a]pyridin-5-yl)acrylonitrile (4.2 g, yield: 65.66%). $^1$H NMR (400 MHz, CHLOROFORM-d) δ 8.42 (s, 1H), 8.03 (d, J=9.3 Hz, 1H), 7.98-7.91 (m, 1H), 7.85-7.78 (m, 1H), 7.60 (d, J=9.2 Hz, 1H).

Step C: (E)-3-(6-iodo-[1,2,4]triazolo[1,5-a]pyridin-5-yl)acrylonitrile (4.50 g, 15.20 mmol), [2-(6-methyl-2-pyridyl)-5,6-dihydro-4H-pyrrolo[1,2-b]pyrazol-3-yl]boronic acid (4.43 g, 18.24 mmol), sodium carbonate (4.83 g, 45.60 mmol), [1,1'-bis(diphenylphosphino)ferrocene]palladium dichloride (556.07 mg, 759.96 μmol), 2-dicyclohexylphosphine-2',6'-dimethoxybiphenyl (311.98 mg, 759.96 μmol) and [2-(2-aminophenyl)phenyl]-chloro-palladium-cyclohexyl-[2-(2,6-dimethoxy) phenyl)phenyl]phosphine (547.64 mg, 759.96 μmol) were added to a mixed solvent of dioxane (100 mL) and water (20 mL). It was charged with nitrogen 3 times and then heated to 90-100° C. and stirred for 2 h. The reaction mixture was quenched with water (200 mL) and extracted with dichloromethane (200 mL×2). The combined organic layers were washed with brine (200 mL), dried over anhydrous sodium sulfate, filtered and concentrated under reduced pressure. The residue was purified by silica gel chromatograph (eluent: dichloromethane/methanol=30/1) to afford crude product, and the crude product was stirred for 12 h in a mixed solvent of petroleum ether/ethyl acetate=5/1, filtered, and the solid was collected and concentrated to give (E)-3-(6-(2-(6-methylpyridin-2-yl)-5,6-dihydro-4H-pyrrolo[1,2-b]pyrazol-3-yl)-[1,2,4]triazolo[1,5-a]pyridin-5-yl)acrylonitrile (5.37 g, yield: 96.16%). $^1$H NMR (400 MHz, CHLOROFORM-d) δ 8.49 (s, 1H), 7.82-7.74 (m, 2H), 7.59-7.46 (m, 4H), 6.99 (dd, J=2.6, 6.1 Hz, 1H), 4.39 (d, J=6.3 Hz, 2H), 2.90-2.70 (m, 4H), 2.20 (s, 3H).

Step D: (E)-3-(6-(2-(6-methylpyridin-2-yl)-5,6-dihydro-4H-pyrrolo[1,2-b]pyrazol-3-yl)-[1,2,4]triazolo[1,5-a]pyridin-5-yl)acrylonitrile (5.37 g, 14.62 mmol) was dissolved in a mixed solvent of dichloromethane (20 mL), dimethyl sulfoxide (70 mL) and water (20 mL), and then hydrogen peroxide (8.29 g, 73.10 mmol, 7.02 mL, 30%) and sodium hydroxide (2 mol/L, 14.62 mL) were added. The mixture was stirred at 15-20° C. for 12 h. The mixture was quenched by pouring into water (200 mL), and extracted with a mixture solvent (200 mL×1) of dichloromethane/isopropyl alcohol (3/1). The organic layer was washed with saturated sodium thiosulfate aqueous solution (200 mL), dried over anhydrous sodium sulfate, filtered and concentrated under reduced pressure. The residue was purified by preparative high performance liquid chromatography (column: Phenomenex Gemini C18 250×50 mm×10 μm; mobile phase: [water (0.05% ammonia v/v)-acetonitrile]; gradient: 5%-32%, 33; 80% min) to give embodiment 1 (3.6 g, yield: 63.82%). $^1$H NMR (400 MHz, CHLOROFORM-d) δ 8.45 (s, 1H), 8.09 (d, J=15.6 Hz, 1H), 7.85 (d, J=15.6 Hz, 1H), 7.69 (d, J=9.2 Hz, 1H), 7.55-7.45 (m, 2H), 7.37 (d, J=7.8 Hz, 1H), 6.99 (d, J=7.7 Hz, 1H), 5.93-5.65 (m, 2H), 4.35 (br. s., 2H), 2.99-2.64 (m, 4H), 2.33 (s, 3H).

Embodiment 2

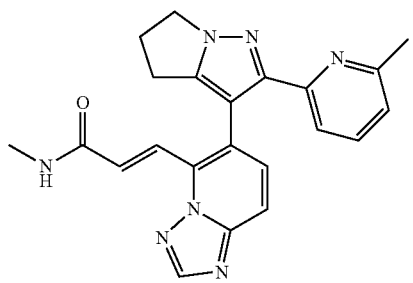

Preparation of Embodiment 2

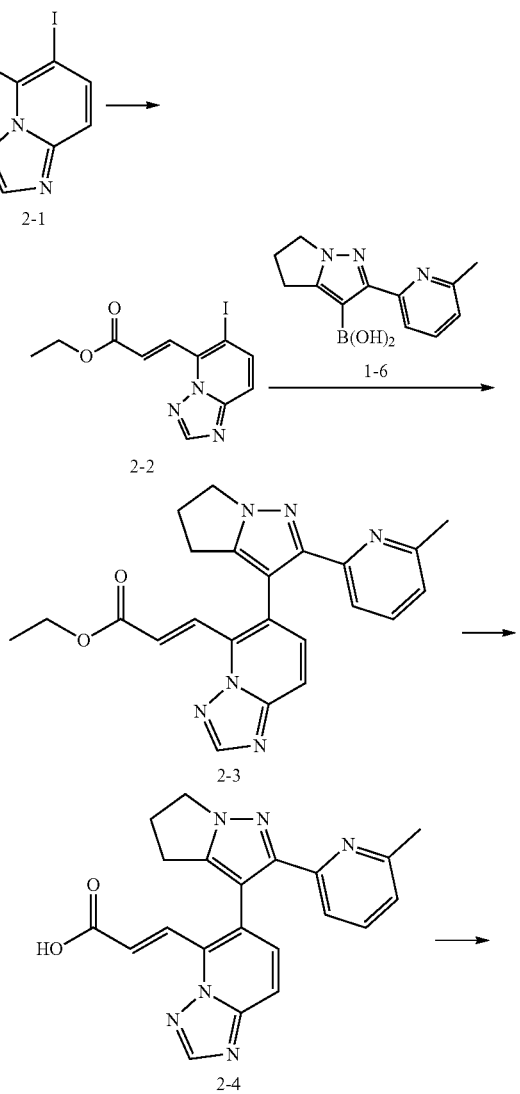

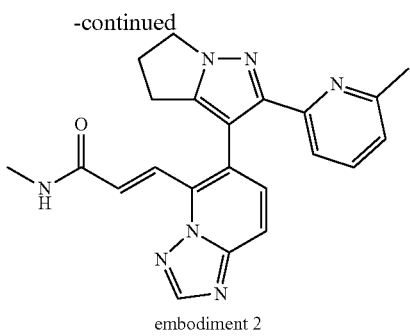

embodiment 2

Step A: ethyl 2-diethoxyphosphorylacetate (295.93 mg, 1.32 mmol, 261.88 μL) was dissolved in tetrahydrofuran (6 mL) and cooled to 0° C., and sodium hydrogen (52.80 mg, 1.32 mmol) was added in one portion. The reaction mixture was stirred at 0° C. for 15 min and then added dropwise to another suspension (6-iodo-[1,2,4]triazolo[1,5-a]pyridine-5-carbaldehyde (300 mg, 1.10 mmol) dispersed in tetrahydrofuran (6 mL) and cooled to −10--15° C.). The reaction mixture was stirred at −10--15° C. for 15 min, quenched by pouring into saturated aqueous ammonium chloride solution (20 mL), and then extracted with dichloromethane (20 mL×3). The combined organic layers were washed with brine (30 mL), dried over anhydrous sodium sulfate, filtered and concentrated under reduced pressure. The residue was purified by silica gel chromatograph (eluent: dichloromethane/ethyl acetate=10/1) to give (E)-ethyl 3-(6-iodo-[1,2,4]triazolo[1,5-a]pyridin-5-yl)acrylate (330 mg, yield: 87.43%).

Step B: (E)-ethyl 3-(6-iodo-[1,2,4]triazolo[1,5-a]pyridin-5-yl)acrylate (330 mg, 961.76 μmol), [2-(6-methyl-2-pyridyl)-5,6-dihydro-4H-pyrrolo[1,2-b]pyrazol-3-yl]boronic acid (268.84 mg, 1.11 mmol), sodium carbonate (305.81 mg, 2.89 mmol), [1,1′-bis(diphenylphosphino)ferrocene]palladium dichloride.dichloromethane (39.27 mg, 48.09 μmol), dicyclohexylphosphine-2′,6′-dimethoxybiphenyl (19.74 mg, 48.09 μmol) and [2-(2-aminophenyl)phenyl]chloro-palladium; cyclohexyl-[2-(2,6-dimethoxyphenyl)phenyl]phosphine (34.65 mg, 48.09 μmol) were added to a mixed solvent of dioxane (10 mL) and water (2 mL). The reaction mixture was charged with nitrogen three times, then heated to 90-100° C. and stirred for 2 h. The reaction mixture was quenched by pouring into water (20 mL), and extracted with dichloromethane (200 mL×3). The combined organic layers were washed with brine, dried over anhydrous sodium sulfate, filtered and concentrated under reduced pressure. The residue was purified by preparative silica gel chromatograph (eluent: dichloromethane/methanol=10/1) to give (E)-ethyl 3-(6-(2-(6-methylpyridin-2-yl)-5,6-dihydro-4H-pyrrolo[1,2-b]pyrazol-3-yl)-[1,2,4]triazolo[1,5-a]pyridin-5-yl)acrylate (359 mg, yield: 81.57%).

Step C: (E)-ethyl 3-(6-(2-(6-methylpyridin-2-yl)-5,6-dihydro-4H-pyrrolo[1,2-b]pyrazol-3-yl)-[1,2,4]triazolo[1,5-a]pyridin-5-yl)acrylate (359.00 mg, 866.19 μmol) was dissolved in a mixed solvent of tetrahydrofuran (6 mL) and water (2 mL), then lithium hydroxide monohydrate (109.04 mg, 2.6 mmol) was added in one portion. The reaction mixture was stirred at 15-20° C. for 12 h, then diluted with water (15 mL) and pH was adjusted to 5-6 with diluted hydrochloric acid (1 mol/L), and then extracted with dichloromethane (20 mL×1). The organic phase was washed with brine (30 mL), dried over anhydrous sodium sulfate, filtered and concentrated under reduced pressure to give (E)-3-(6-(2-(6-methylpyridin-2-yl)-5,6-dihydro-4H-pyrrolo[1,2-b]pyrazol-3-yl)-[1,2,4]triazolo[1,5-a]pyridin-5-yl)acrylic acid (330 mg, yield: 98.59%).

Step D: (E)-3-(6-(2-(6-methylpyridin-2-yl)-5,6-dihydro-4H-pyrrolo[1,2-b]pyrazol-3-yl)-[1,2,4]triazolo[1,5-a]pyridin-5-yl)acrylic acid (65 mg, 168.22 μmol), methylamine hydrochloride (22.72 mg, 336.44 μmol), HATU (127.92 mg, 336.44 μmol) and triethylamine (68.09 mg, 672.88 μmol, 93.27 μL) were dissolved in N,N-dimethylformamide (2 mL). The reaction mixture was stirred at 15-20° C. for 12 h, diluted directly with methanol (2 mL) and purified by preparative high performance liquid chromatography (column: Phenomenex Gemini 150×25 mm×10 μm; mobile phase: [water (0.05) % ammonia water v/v)-acetonitrile]; gradient: 21%-51%, 15 min) to give embodiment 2 (27.79 mg, yield: 41.36%). $^1$H NMR (400 MHz, DMSO-d6) δ 8.67 (s, 1H), 8.43 (d, J=4.6 Hz, 1H), 7.93-7.80 (m, 2H), 7.68-7.61 (m, 2H), 7.60-7.49 (m, 2H), 7.02 (dd, J=1.6, 6.8 Hz, 1H), 4.29 (d, J=9.0 Hz, 2H), 2.84-2.72 (m, 2H), 2.69-2.57 (m, 5H), 1.99 (s, 3H).

Embodiment 3 to 5 Can Be Prepared According to the Preparation Process of Embodiment 2

Embodiment 3

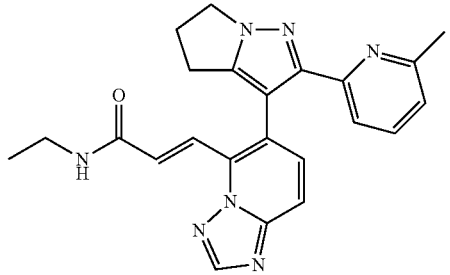 [SMILES: CCNC(=O)/C=C/c1c(-c2c(-c3cccc(C)n3)nn3c2CCC3)ccc2ncnn12]

$^1$H NMR (400 MHz, DMSO-d6) δ 8.67 (s, 1H), 8.48 (br t, J=5.3 Hz, 1H), 7.95-7.78 (m, 2H), 7.69-7.46 (m, 4H), 7.02 (dd, J=1.6, 6.7 Hz, 1H), 4.29 (br d, J=7.5 Hz, 2H), 3.26-3.08 (m, 2H), 2.81-2.58 (m, 4H), 1.99 (s, 3H), 1.04 (t, J=7.2 Hz, 3H).

Embodiment 4

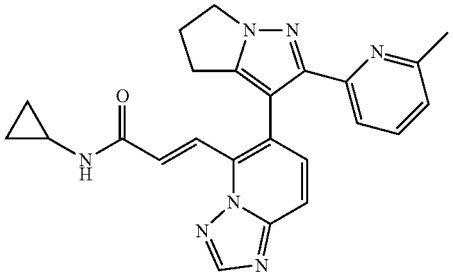 [SMILES: Cc1cccc(-c2nn3c(c2-c2ccc4ncnn4c2/C=C/C(=O)NC2CC2)CCC3)n1]

$^1$H NMR (400 MHz, DMSO-d6) δ 8.66 (s, 1H), 8.53 (d, J=4.8 Hz, 1H), 8.14 (s, 1H), 7.89-7.81 (m, 2H), 7.69-7.61 (m, 2H), 7.60-7.48 (m, 2H), 7.06-7.00 (m, 1H), 4.30 (d, J=8.9 Hz, 2H), 2.83-2.73 (m, 3H), 2.66-2.60 (m, 2H), 1.99 (s, 3H), 0.65 (d, J=5.6 Hz, 2H), 0.46 (d, J=2.8 Hz, 2H).

Embodiment 5

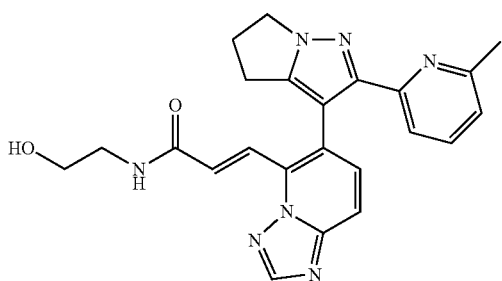 [SMILES: Cc1cccc(-c2nn3c(c2-c2ccc4ncnn4c2/C=C/C(=O)NCCO)CCC3)n1]

$^1$H NMR (400 MHz, DMSO-d6) δ 8.67 (s, 1H), 8.50 (t, J=5.6 Hz, 1H), 7.93 (d, J=15.6 Hz, 1H), 7.83 (d, J=9.2 Hz, 1H), 7.69-7.61 (m, 2H), 7.59-7.49 (m, 2H), 7.02 (dd, J=1.8, 6.7 Hz, 1H), 4.69 (t, J=5.5 Hz, 1H), 4.34-4.24 (m, 2H), 3.43 (q, J=5.9 Hz, 2H), 3.21 (d, J=3.1 Hz, 2H), 2.83-2.73 (m, 2H), 2.62 (quin, J=7.2 Hz, 2H), 1.99 (s, 3H).

Embodiment 6

Preparation of Intermediate 6-4

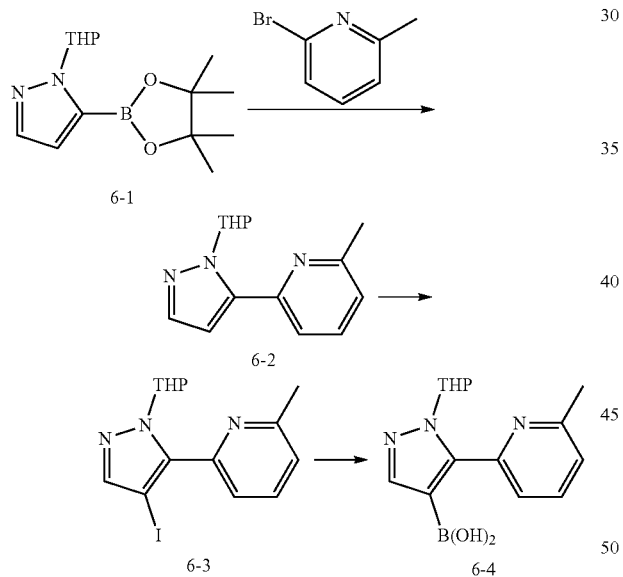

Step A: 1-tetrahydropyran-2-yl-5-(4,4,5,5-tetramethyl-1,3,2-dioxaborolan-2-yl)pyrazole (10.96 g, 39.41 mmol), 2-bromo-6-methyl-pyridine (6.00 g, 34.88 mmol, 3.97 mL), [1,1'-bis(diphenylphosphino)ferrocene]palladium dichloride (1.28 g, 1.74 mmol) and sodium carbonate (11.09 g, 104.64 mmol) were added to a mixed solvent of dioxane (200.00 mL) and water (40.00 mL). The reaction mixture was charged with nitrogen three times, then heated to 80-90° C. and stirred for 3 h, then quenched by pouring into water (200 mL), and extracted with ethyl acetate (180 mL×2). The combined organic phase was washed with brine (200 mL), dried over anhydrous sodium sulfate, filtered and concentrated under reduced pressure. The residue was purified by silica gel chromatograph (eluent: petroleum ether/ethyl acetate=10/1-5/1) to give 2-methyl-6-(1-(tetrahydro-2H-pyran-2-yl)-1H-pyrazol-5-yl)pyridine (4.10 g, crude). The product was identified as crude by nuclear magnetics.

Step B: 2-methyl-6-(1-(tetrahydro-2H-pyran-2-yl)-1H-pyrazol-5-yl)pyridine (2.10 g, crude) was dissolved in acetic acid (20.00 mL), then NIS (2.04 g, 9.06 mmol) was added in one portion. The mixture was heated to 70-80° C. and stirred for 1 h, then quenched by pouring into a saturated sodium bicarbonate solution (50 mL) and then extracted with ethyl acetate (50 mL×3). The combined organic phase was washed with brine (30 mL), dried over anhydrous sodium sulfate, filtered and concentrated under reduced pressure. The residue was purified by silica gel chromatograph (eluent: petroleum ether/ethyl acetate=10/1) to give 2-(4-iodo-1-(tetrahydro-2H-pyran-2-yl)-1H-pyrazol-5-yl)-6-methylpyridine (1.60 g, yield: 50.22%).

Step C: 2-(4-iodo-1-(tetrahydro-2H-pyran-2-yl)-1H-pyrazol-5-yl)-6-methylpyridine (500.00 mg, 1.35 mmol) and triisopropyl borate (672.82 mg, 3.58 mmol, 820.51 μL) was dissolved in tetrahydrofuran (10 mL). The reaction mixture was cooled to −78° C., n-butyllithium (2.5 M, 1.40 mL) was added dropwise and stirred at −78--60° C. for 30 min. The reaction mixture was quenched by pouring into saturated ammonium chloride solution, stirred for 10 min, and extracted with ethyl acetate (20 mL×2). The combined organic phase was dried over anhydrous sodium sulfate, filtered and concentrated under reduced pressure. The residue was purified by preparative silica gel chromatograph (eluent: petroleum ether/ethyl acetate=1/1) to give (5-(6-methylpyridin-2-yl)-1-(tetrahydro-2H-pyran-2-yl)-1H-pyrazol-4-yl)boronic acid (200.00 mg, yield: 51.60%).

Preparation of Embodiment 6

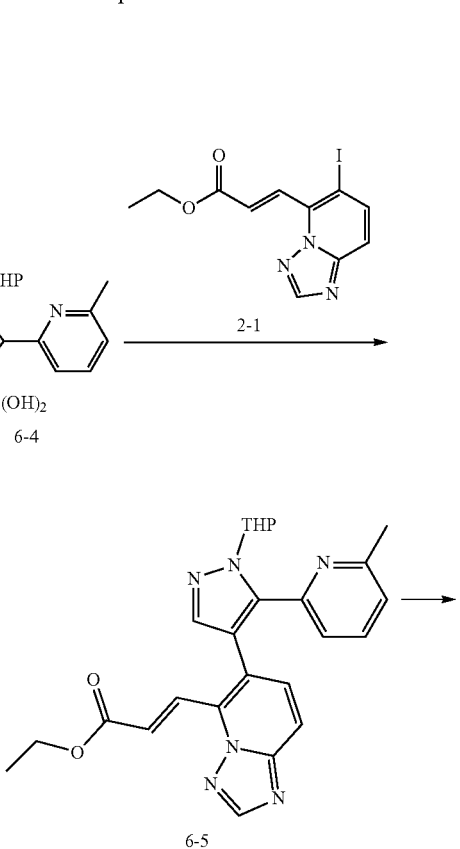

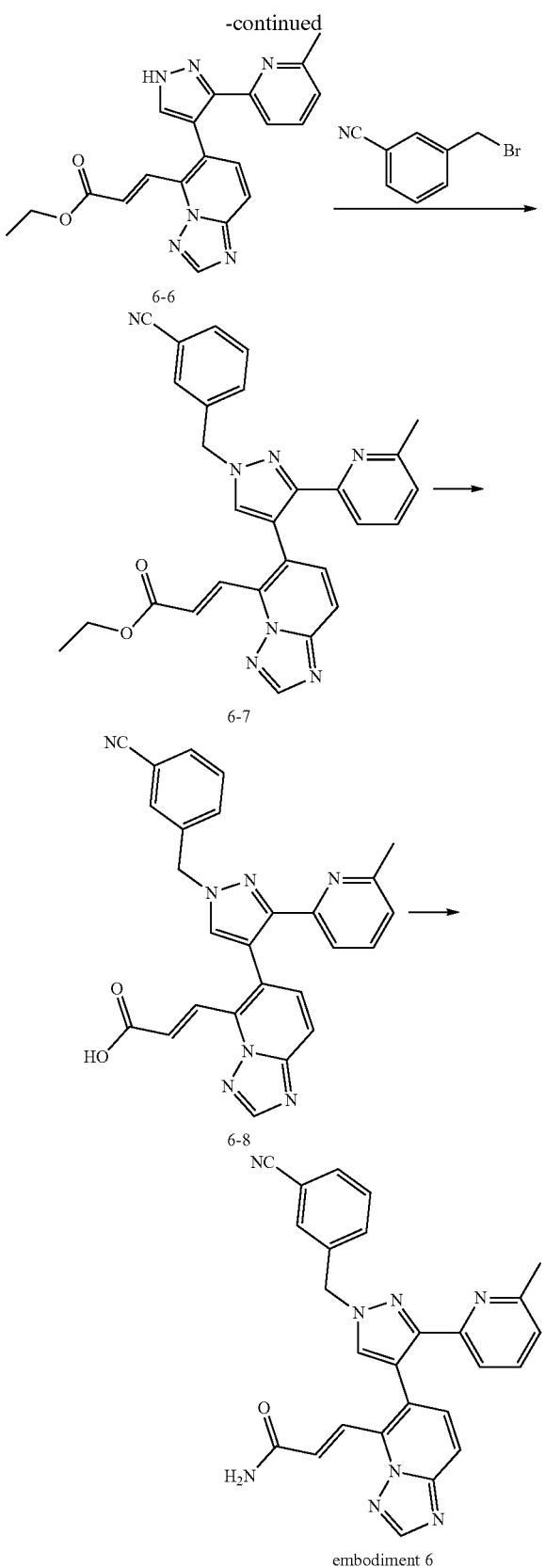

Step A: [5-(6-methyl-2-pyridyl)-1-tetrahydropyran-2-yl-pyrazol-4-yl]boronic acid (200.00 mg, 696.57 µmol), (E)-ethyl 3-(6-iodo-[1,2,4]triazolo[1,5-a]pyridin-5-yl)acrylate (239.01 mg, 696.57 µmol), sodium carbonate (221.49 mg, 2.09 mmol), [1,1'-bis(diphenylphosphino)ferrocene]palladium dichloride (50.97 mg, 69.66 µmol), dicyclohexylphosphine-2',6'-dimethoxybiphenyl (28.60 mg, 69.66 µmol) and [2-(2-aminophenyl)phenyl]-chloro-palladium; cyclohexyl-[2-(2,6-dimethoxyphenyl)phenyl]phosphine (50.20 mg, 69.66 µmol) were added to a mixed solvent of dioxane (3 mL) and water (1 mL). It was charged with nitrogen 3 times, then heated to 80-90° C. and stirred for 3 h. The reaction mixture was quenched by pouring into water (30 mL), and extracted with ethyl acetate (30 mL×2). The combined organic phase was dried over anhydrous sodium sulfate, filtered and concentrated under reduced pressure. The residue was purified by preparative silica gel chromatograph (eluent: dichloromethane/methanol=30/1) to afford (E)-ethyl 3-(6-(5-(6-methylpyridin-2-yl)-1-(tetrahydro-2H-pyran-2-yl)-1H-pyrazol-4-yl)-[1,2,4]triazolo[1,5-a]pyridin-5-yl)acrylate (250.00 mg, yield: 78.27%).

Step B: (E)-ethyl 3-(6-(5-(6-methylpyridin-2-yl)-1-(tetrahydro-2H-pyran-2-yl)-1H-pyrazol-4-yl)-[1,2,4]triazolo[1,5-a]pyridin-5-yl)acrylate (250.00 mg, 545.24 µmol) was dissolved in ethanol (3 mL), then dioxane hydrochloride (4M, 5.01 mL) was added. The reaction mixture was stirred at 15-20° C. for 12 h, evaporated to remove the solvent, and then was adjusted to pH of 8-9 with saturated sodium bicarbonate solution (20 mL) and extracted with dichloromethane (20 mL×2). The combined organic phases were washed with brine (30 mL), dried over anhydrous sodium sulfate, filtered and concentrated under reduced pressure to give (E)-ethyl 3-(6-(3-(6-methylpyridin-2-yl)-1H-pyrazol-4-yl)-[1,2,4]triazolo[1,5-a]pyridin-5-yl)acrylate (230.00 mg, crude).

Step C: (E)-ethyl 3-(6-(3-(6-methylpyridin-2-yl)-1H-pyrazol-4-yl)-[1,2,4]triazolo[1,5-a]pyridin-5-yl)acrylate was dissolved in THF (5 mL). The reaction mixture was cooled to −20° C. and then sodium hydrogen (27.03 mg, 675.75 µmol) was added, and stirred at −20° C. for 30 min. Then 3-cyanobenzyl bromide (132.47 mg, 675.75 µmol) was added. The reaction mixture was warmed to 15-20° C. and was further stirred for 4 h, then quenched by pouring into water (20 mL), adjusted to pH of 5-6 with dilute aqueous hydrochloric acid (1M), and extracted with ethyl acetate (20 mL). The combined organic phases were dried over anhydrous sodium sulfate, filtered and concentrated under reduced pressure. The residue was purified by preparative silica gel chromatograph (eluent: dichloromethane/methanol=30/1) to afford (E)-ethyl 3-(6-(1-(3-cyanobenzyl)-3-(6-methylpyridin-2-yl)-1H-pyrazol-4-yl)-[1,2,4]triazolo[1,5-a]pyridin-5-yl)acrylate (150.00 mg, yield: 46.67%).

Step D: (E)-ethyl 3-(6-(1-(3-cyanobenzyl)-3-(6-methylpyridin-2-yl)-1H-pyrazol-4-yl)-[1,2,4]triazolo[1,5-a]pyridin-5-yl)acrylate (150.00 mg, 306.42 µmol) was dissolved in tetrahydrofuran (3 mL), then lithium hydroxide monohydrate (38.57 mg, 919.26 µmol) was added in one portion. The reaction mixture was stirred at 15-20° C. for 12 h, then quenched by pouring to water (10 mL), and adjusted to pH of 5-6 with dilute aqueous hydrochloric acid (1M), then extracted with dichloromethane (20 mL×2). The combined organic phases were washed with brine (30 mL), dried over anhydrous sodium sulfate, filtered and concentrated under reduced pressure to give (E)-3-(6-(1-(3-cyanobenzyl)-3-(6-methylpyridin-2-yl)-1H-pyrazol-4-yl)-[1,2,4]triazolo[1,5-a]pyridin-5-yl)acrylic acid (130.00 mg, yield: 91.94%).

Step E: (E)-3-(6-(1-(3-cyanobenzyl)-3-(6-methylpyridin-2-yl)-1H-pyrazol-4-yl)-[1,2,4]triazolo[1,5-a]pyridin-5-yl)acrylic acid (130.00 mg, 281.71 µmol), HATU (214.23 mg, 563.42 µmol) and triethylamine (57.01 mg, 563.42 µmol, 78.10 μL) were dissolved in N,N-dimethylformamide (2 mL). After the reaction mixture was stirred at 15-20° C. for 1 h, a solution of 3 mL of ammonia in tetrahydrofuran (saturated at 0° C.) was added. The reaction mixture was further stirred at 15-20° C. for 30 min, concentrated under reduced pressure to remove the solvent and then diluted with methanol (2 mL). The residue was purified by high preparative performance liquid chromatography (column: Phenomenex Synergi C18 150×30 mm×4 μm; mobile phase: [water (0.225% formic acid)-acetonitrile]; gradient: 15%-45%, 12 min) to give embodiment 6 (53.00 mg, yield: 40.32%). ¹H NMR (400 MHz, DMSO-d6) δ 8.69 (s, 1H), 8.25 (s, 1H), 7.93-7.81 (m, 5H), 7.67-7.52 (m, 6H), 7.24 (br. s., 1H), 7.04 (dd, J=2.0, 6.2 Hz, 1H), 5.61 (s, 2H), 1.98 (s, 3H).

Embodiment 7 can be Prepared According to the Preparation Process of Embodiment 6

Embodiment 7

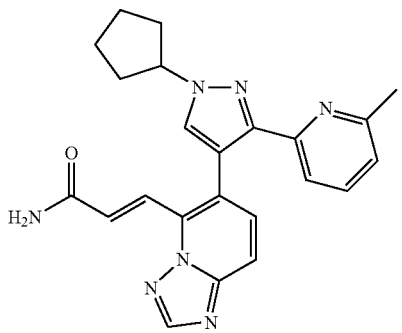 [SMILES: Cc1cccc(-c2nn(C3CCCC3)cc2-c2ccc3ncnn3c2/C=C/C(N)=O)n1]

¹H NMR (400 MHz, DMSO-d6) δ 8.67 (s, 1H), 8.41-8.36 (m, 1H), 8.38 (s, 1H), 8.09 (s, 1H), 7.89-7.78 (m, 3H), 7.69-7.58 (m, 3H), 7.51 (d, J=15.7 Hz, 1H), 7.16 (br s, 1H), 7.02 (d, J=6.8 Hz, 1H), 4.86 (quin, J=6.9 Hz, 1H), 2.22-2.16 (m, 2H), 2.14-2.04 (m, 2H), 1.97 (s, 3H), 1.92-1.83 (m, 2H), 1.76-1.66 (m, 2H).

Embodiment 8

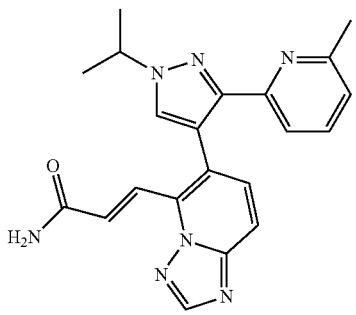 [SMILES: Cc1cccc(-c2nn(C(C)C)cc2-c2ccc3ncnn3c2/C=C/C(N)=O)n1]

Preparation of Intermediate 8-2

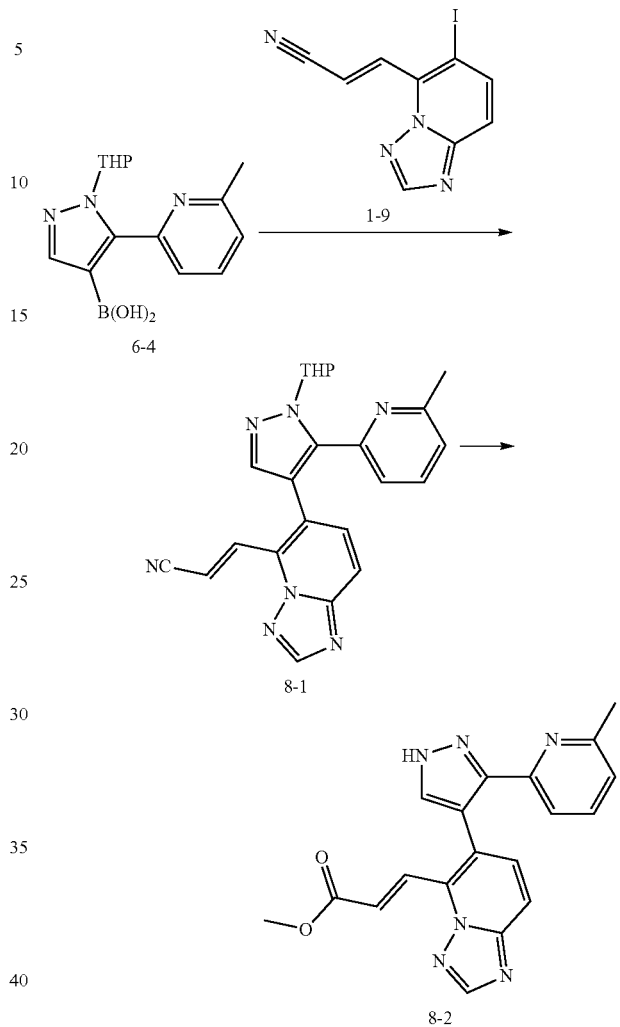

Step A: [5-(6-methyl-2-pyridyl)-1-tetrahydropyran-2-yl-pyrazol-4-yl]boronic acid (470.00 mg, 1.64 mmol), (E)-3-(6-iodo-[1,2,4]triazolo[1,5-a]pyridin-5-yl)acrylonitrile (485.55 mg, 1.64 mmol), sodium carbonate (521.47 mg, 4.92 mmol, [1,1'-bis(diphenylphosphino)ferrocene]palladium dichloride (36.00 mg, 49.20 μmol), biscyclohexylphosphino-2'6'-dimethoxybiphenyl (6.73 mg, 16.40 μmol) and [2-(2-aminophenyl) phenyl]-chloro-palladium; cyclohexyl-[2-(2,6-dimethoxyphenyl)phenyl]phosphine (11.82 mg, 16.40 μmol) were added to a mixed solvent of dioxane (20 mL) and water (5 mL). The reaction mixture was charged with nitrogen for 3 times, then heated to 80-90° C. and stirred for 12 h, then quenched by pouring into water (30 mL) and extracted with ethyl acetate (30 mL×2). The combined organic phases were dried over anhydrous sodium sulfate, filtered and concentrated under reduced pressure. The obtained crude product was stirred for 30 min in a mixed solvent of petroleum ether (12 mL) and ethyl acetate (4 mL) and filtered. The solid was collected and concentratedunder reduced pressure to give (E)-3-(6-(5-(6-methylpyridin-2-yl)-1-(tetrahydro-2H-pyran-2-yl)-1H-pyrazol-4-yl)-[1,2,4]triazolo[1,5-a]pyridin-5-yl)acrylonitrile (554.00 mg, yield: 82.32%).

Step B: (E)-3-(6-(5-(6-methylpyridin-2-yl)-1-(tetrahydro-2H-pyran-2-yl)-1H-pyrazol-4-yl)-[1,2,4]triazolo[1,5-a]pyridin-5-yl)acrylonitrile (554.00 mg, 1.35 mmol) was dissolved in methanol (5 mL), then dioxane hydrochloride (4 mol/L, 5 mL) was added. The reaction mixture was stirred at 15-20° C. for 12 h, concentrated under reduced pressure to remove solvent, and adjusted to pH of 8-9, then extracted with dichloromethane (20 mL×2). The combined organic phases were washed with brine (30 mL), dried over anhydrous sodium sulfate, filtered and concentrated under reduced pressure to give (E)-methyl 3-(6(3-(6-methylpyridin-2-yl)-1H-pyrazol-4-yl)[1,2,4]triazolo[1,5-a]pyridin-5-yl)acrylate (500.00 mg, crude).

Preparation of Embodiment 8

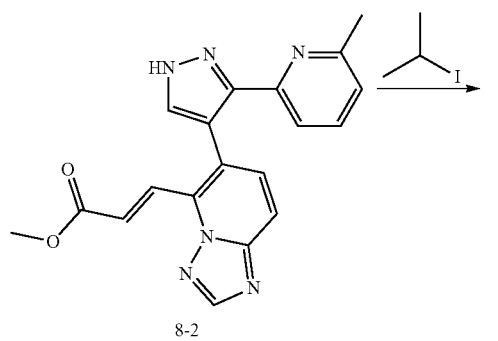

8-2

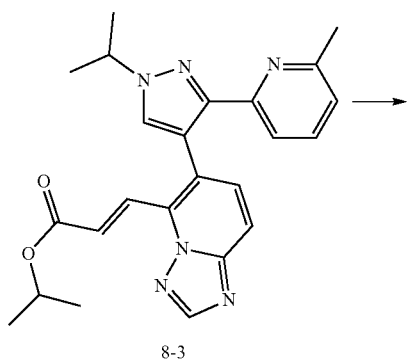

8-3

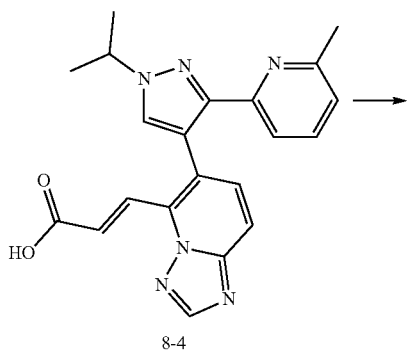

8-4

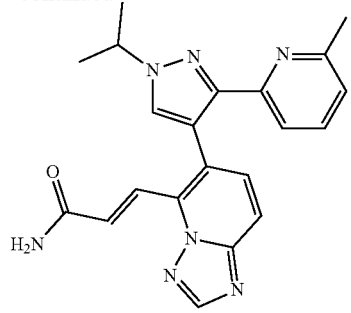

embodiment 8

Step A: (E)-methyl 3-(6-(3-(6-methylpyridin-2-yl)-1H-pyrazol-4-yl)-[1,2,4]triazolo[1,5-a]pyridin-5-yl)acrylate (260.00 mg, crude) was dissolved in tetrahydrofuran (4 mL). The reaction mixture was cooled to 0° C., sodium hydrogen (31.75 mg, 793.63 μmol) was added in one portion, and then stirred at 0° C. for 30 min, then iodoisopropane (134.91 mg, 793.63 μmol) was added. The reaction mixture was stirred at 15-20° C. for 12 h. LCMS monitoring showed (E)-methyl 3-(6-(3-(6-methylpyridin-2-yl)-1H-pyrazol-4-yl)-[1,2,4]triazolo[1,5-a]pyridin-5-yl) acrylate was consumed completely, but the target product was not formed (MS (ESI) m/z: 347 [M+H$^+$]). The mixture was concentrated under reduced pressure to remove tetrahydrofuran, and the residue was dissolved in N,N-dimethylformamide (3 mL), then 2-iodoisopropane (613.22 mg, 3.61 mmol, 360.72 μL) and potassium (498.58 mg, 3.61 mmol) were added. The reaction mixture was stirred for another 12 h at 15-20° C. LCMS monitoring indicated completion of the reaction. The mixture was quenched by pouring into water (20 mL) and then extracted with ethyl acetate (30 ml×3). The combined organic phases were washed with brine (60 mL), dried over anhydrous sodium sulfate, filtered and concentrated under reduced pressure. The residue was purified by preparative silica gel chromatography (eluent: methylene chloride/methanol=30/1) to afford (E)-isopropyl 3-(6-(1-isopropyl-3-(6-methylpyridin-2-yl)-1H-pyrazol-4-yl)-[1,2,4]triazolo[1,5-a]pyridin-5-yl)acrylate (100.00 mg, crude).

Step B: (E)-isopropyl 3-(6-(1-isopropyl-3-(6-methylpyridin-2-yl)-1H-pyrazol-4-yl)-[1,2,4]triazolo[1,5-a]pyridin-5-yl)acrylate (100.00 mg, crude) was dissolved in a mixed solvent of tetrahydrofuran (1 mL), methanol (1 mL) and water (1 mL), lithium hydroxide monohydrate (29.24 mg, 696.87 μmol) was then added in one portion. The reaction mixture was stirred at 15-20° C. for 3 h, then adjusted to pH of 5-6 with dilute hydrochloric acid (5%) and extracted with ethyl acetate (20 mL×3). The combined organic phases were washed with brine (30 mL), dried over anhydrous sodium sulfate, filtered and concentrated under reduced pressure to give (E)-3-(6-(1-isopropyl-3-(6-m ethylpyridin-2-yl)-1H-pyrazol-4-yl)-[1,2,4]triazolo[1,5-a]pyridin-5-yl)acrylic acid (100.00 mg, crude).

Step C: (E)-3-(6-(1-isopropyl-3-(6-methylpyridin-2-yl)-1H-pyrazol-4-yl)-[1,2,4]triazolo[1,5-a]pyridin-5-yl)acrylic acid (100.00 mg, crude) was dissolved in tetrahydrofuran (3 mL), then HATU (195.78 mg, 514.90 μmol) and triethylamine (52.10 mg, 514.90 μmol, 71.37 μL) were added in one portion respectively. After the reaction mixture was stirred at 15-20° C. for 1 h, a solution of 3 mL of ammonia in tetrahydrofuran (saturated at 0° C.) was added. The reaction mixture was further stirred at 15-20° C. for 12 h. The solvent was concentrated under reduced pressure to remove the solvent and diluted with methanol (3 mL), and then purified by preparative high performance liquid chromatography (column: Phenomenex Synergi C18 150×30 mm×4 μm; mobile phase: [water (0.225% formic acid)-acetonitrile]; gradient: 10%-40%, 12 min) embodiment 8 (30.50 mg, yield: 30.08%). $^1$H NMR (400 MHz, DMSO-d6) δ 8.68 (s, 1H), 8.10 (s, 1H), 7.89-7.81 (m, 3H), 7.68-7.59 (m, 3H), 7.51 (d, J=15.7 Hz, 1H), 7.18 (br s, 1H), 7.02 (dd, J=1.2, 7.1 Hz, 1H), 4.67 (quin, J=6.7 Hz, 1H), 1.97 (s, 3H), 1.55 (d, J=6.7 Hz, 6H).

Embodiment 9

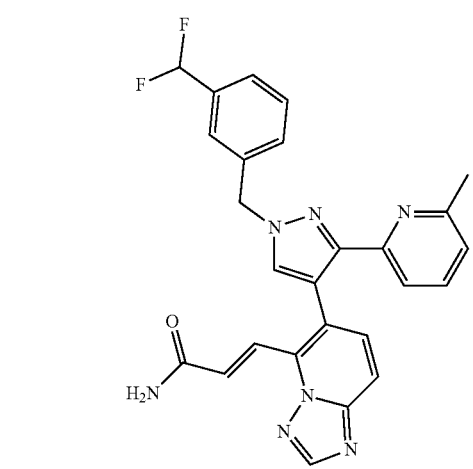 [SMILES: Cc1cccc(-c2nn(Cc3cccc(C(F)F)c3)cc2-c2ccc3ncnn3c2/C=C/C(N)=O)n1]

Preparation of Embodiment 9

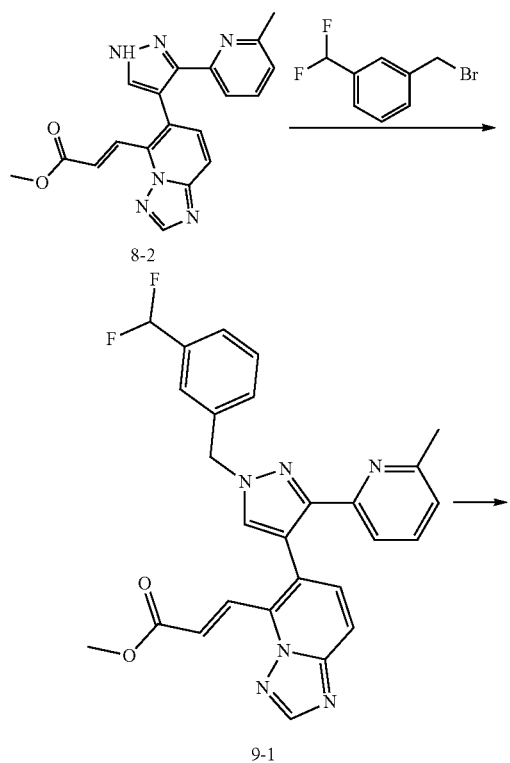

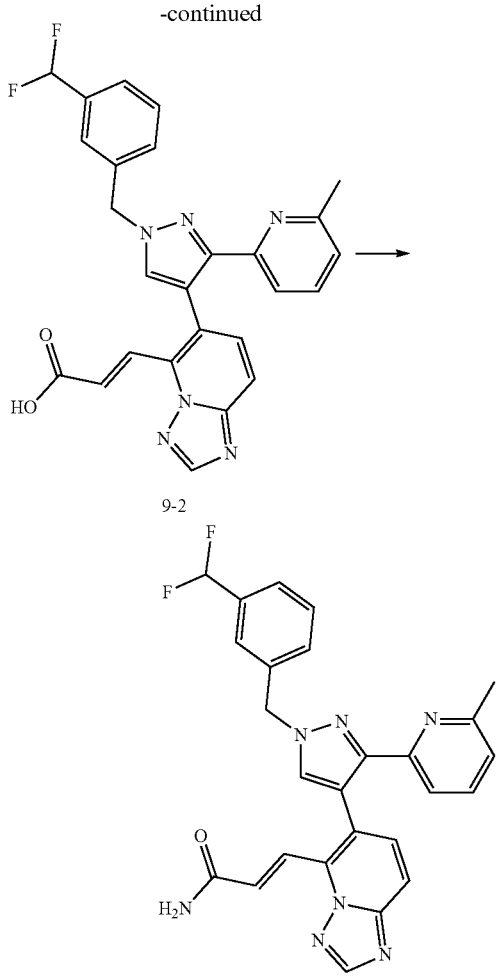

embodiment 9

Step A: (E)-methyl 3-(6-(3-(6-methylpyridin-2-yl)-1H-pyrazol-4-yl)-[1,2,4]triazolo[1,5-a]pyridin-5-yl)acrylate (200.00 mg, crude) was dissolved in tetrahydrofuran (5 mL). After cooling to 0° C., sodium hydrogen (24.42 mg, 610.49 μmol) was added in one portion. The reaction mixture was stirred at 0° C. for 30 min, then 1-(bromomethyl)-3-(difluoromethyl) benzene (134.94 mg, 610.49 μmol) was added, then the reaction mixture was warmed to 15-20° C. and further stirred for 5 h. The reaction mixture was quenched by pouring into water (20 mL) and extracted with ethyl acetate (20 mL×3). The combined organic phases were washed brine (30 mL), dried over anhydrous sodium sulfate, filtered and concentrated under reduced pressure to give (E)-methyl 3-(6-(1-(3-(difluoromethyl)benzyl)-3-(6-methylpyridin-2-yl)-1H-pyrazol-4-yl)-[1,2,4]triazolo[1,5-a]pyridin-5-yl)acrylate (150.00 mg, crude).

Step B: (E)-methyl 3-(6-(1-(3-(difluoromethyl)benzyl)-3-(6-methylpyridin-2-yl)-1H-pyrazol-4-yl)-[1,2,4]triazolo[1,5-a]pyridin-5-yl)acrylate (150.00 mg, crude) was dissolved in a mixed solvent of tetrahydrofuran (1 mL), methanol (1 mL) and water (1 mL), then lithium hydroxide monohydrate (37.73 mg, 899.10 μmol) was added in one portion. The reaction mixture was stirred at 15-20° C. for 10 min, and adjusted to pH of 5-6 with dilute hydrochloric acid (0.5M), at which time solids precipitated. The solid was filtered and collected to give (E)-3-(6-(1-(3-(difluoromethyl)benzyl)-3-

(6-methylpyridin-2-yl)-1H-pyrazol-4-yl)-[1,2,4]triazolo[1,5-a]pyridin-5-yl)acrylic acid (120.00 mg, yield: 60.34%).

Step C: (E)-3-(6-(1-(3-(difluoromethyl)benzyl)-3-(6-methylpyridin-2-yl)-1H-pyrazol-4-yl)-[1,2,4]triazolo[1,5-a]pyridin-5-yl)acrylic acid (120.00 mg, 180.83 μmol), HATU (187.59 mg, 493.36 μmol) and triethylamine (49.92 mg, 493.36 μmol, 68.38 μL) were dissolved in tetrahydrofuran (3 mL). The reaction mixture was stirred at 15-20° C. for 1 h, then 3 mL of a solution of ammonia in tetrahydrofuran (saturated at 0° C.) was added. The reaction mixture was stirred at 15-20° C. for 12 h then quenched by pouring to water and extracted with ethyl acetate (20 mL×3). The combined organic phases were washed with brine (50 mL), dried over anhydrous sodium sulfate, filtered and concentrated under reduced pressure. The residue was purified by preparative high performance liquid chromatography (column: Phenomenex Synergi C18 150×30 mm×4 μm; mobile phase: [water (0.225% formic acid)-acetonitrile]; gradient 15%-45%, 12 min) embodiment 9 (47.85 mg, yield: 39.81%). $^1$H NMR (400 MHz, DMSO-d6) δ 8.70 (s, 1H), 8.26 (s, 1H), 7.95-7.83 (m, 3H), 7.67-7.51 (m, 8H), 7.28 (d, J=11.2 Hz, 1H), 7.07-6.96 (m, 1H), 7.12 (s, 1H), 5.61 (s, 2H), 1.97 (s, 3H).

Embodiment 10

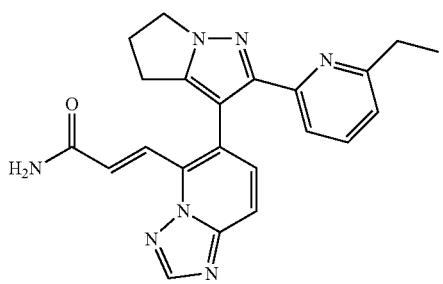 [SMILES: CCc1cccc(-c2nn3c(c2-c2ccc4ncnn4c2/C=C/C(N)=O)CCC3)n1]

Preparation of Intermediate 10-3

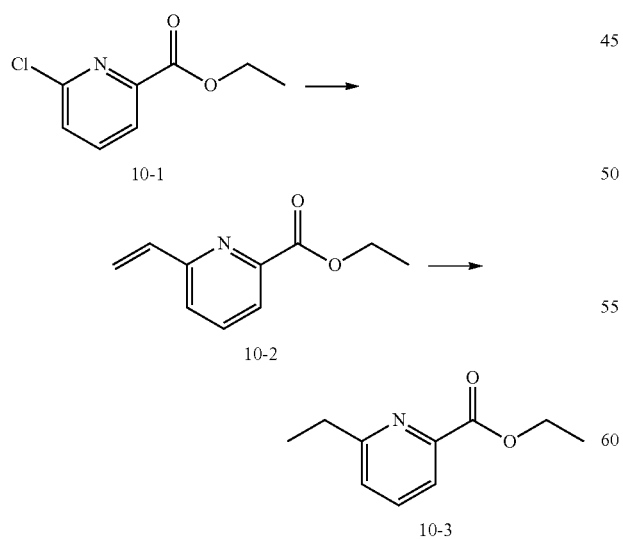

Step A: ethyl 6-chloropyridine-2-carboxylate (500.00 mg, 2.69 mmol), vinyl tributyltin (887.12 mg, 2.80 mmol, 813.87 μL) and tetrakis(triphenylphosphine)palladium (155.42 mg, 134.50 μmol) were dissolved in toluene (10 mL). The reaction mixture was charged with nitrogen three times, then heated to 110-120° C. and stirred for 3 h. After cooling, it was poured into a saturated potassium fluoride solution (30 mL) and stirred for 30 min. The mixture was filtered, and the filter cake was washed with ethyl acetate (10 mL×3). The filtrate was extracted with ethyl acetate (30 mL×2). The combined organic phases were washed with brine (50 mL), dried over anhydrous sodium sulfate, filtered and concentrated under reduced pressure. The residue was purified by silica gel chromatograph (eluent: petroleum ether/ethyl acetate=10/1) to give ethyl 6-vinylpyridine-2-carboxylate (364.00 mg, yield: 76.21%). $^1$H NMR (400 MHz, CHLOROFORM-d) 8.00 (dd, J=0.8, 7.8 Hz, 1H), 7.81 (t, J=7.8 Hz, 1H), 7.61 (dd, J=0.9, 7.9 Hz, 1H), 6.96 (dd, J=10.9, 17.6 Hz, 1H), 6.25 (dd, J=0.6, 17.6 Hz, 1H), 5.67-5.56 (m, 1H), 4.50 (q, J=7.2 Hz, 2H), 1.46 (t, J=7.2 Hz, 3H).

Step B: ethyl 6-vinylpyridine-2-carboxylate (364.00 mg, 2.05 mmol) was dissolved in ethanol (4 mL) and then palladium carbon (40.00 mg, 10%) was added in one portion. The reaction mixture was charged with hydrogen three times and then stirred at 15-20° C. for 3 h under 15 psi hydrogen pressure. Subsequently, palladium carbon was removed by filtration, and the filtrate was concentrated under reduced pressure to give ethyl 6-ethylpyridine-2-carboxylate (320.00 mg, yield: 87.10%). $^1$H NMR (400 MHz, CHLOROFORM-d) 7.95 (d, J=7.7 Hz, 1H), 7.75 (t, J=7.8 Hz, 1H), 7.37 (d, J=7.8 Hz, 1H), 4.49 (q, J=7.1 Hz, 2H), 2.96 (q, J=7.7 Hz, 2H), 1.44 (t, J=7.2 Hz, 3H), 1.34 (t, J=7.7 Hz, 3H).

Embodiment 10 can be Prepared According to the Preparation Process of Embodiment 1

$^1$H NMR (400 MHz, DMSO-d$_6$) δ 8.66 (s, 1H), 7.81-7.91 (m, 3H), 7.61-7.72 (m, 2H), 7.57 (d, J=9.03 Hz, 1H), 7.49 (d, J=15.69 Hz, 1H), 7.21 (br s, 1H), 6.96-7.03 (m, 1H), 4.21-4.37 (m, 2H), 2.70-2.92 (m, 2H), 2.62 (q, J=7.18 Hz, 2H), 2.27 (q, J=7.53 Hz, 2H), 0.48 (t, J=7.53 Hz, 3H).

Embodiment 11

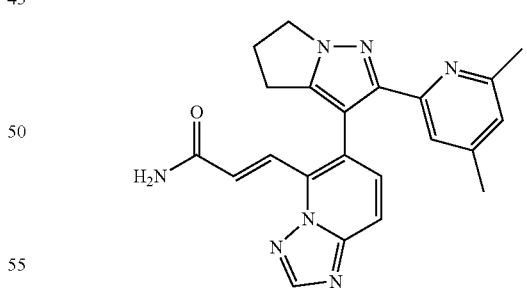

Preparation of Intermediate 11-2

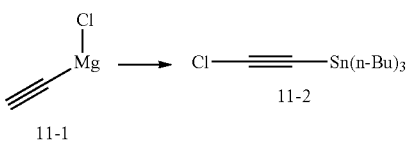

Step A: tri-n-butyltin chloride (72.09 mL, 268.00 mmol) was added dropwise (not less than 30 min) to a solution of ethynylmagnesium chloride in tetrahydrofuran (0.5 mol/L, 800.00 mL) while stirring at 0° C. The reaction mixture was stirred at 30° C. for 0.5 h, then warmed to 35° C. and stirred for 1 h. After that, it was cooled to 0° C., and then quenched with aqueous ammonium chloride (800 mL), then extracted with petroleum ether (800 mL×2). The combined organic phases were washed with brine (400 mL), dried over anhydrous sodium sulfate, filtered and concentrated under reduced pressure to give tributyl(chloroethynyl)stannane (84.00 g, yield: 60.08%). $^1$H NMR (400 MHz, CHLOROFORM-d) δ: 1.54-1.67 (m, 6H), 1.32-1.35 (m, 6H), 0.88-1.04 (m, 15H).

Preparation of Intermediate 11-6

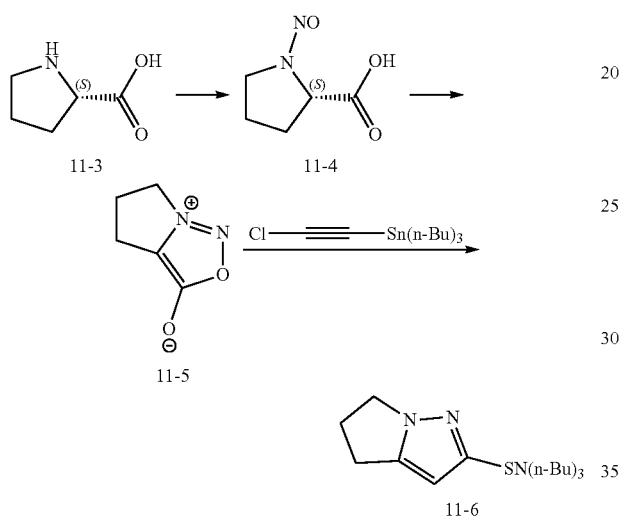

Step A: L-proline (50 g, 434.29 mmol) and sodium nitrite (41.95 g, 608.01 mmol) were dissolved in water, then concentrated hydrochloric acid (50 mL) was added at −10-0° C. (controlled to be no higher than 10° C.). After the addition was completed, the reaction mixture was stirred at 0° C. for 0.5 h, then raised to 25° C. and stirred for 16 h. The mixture was diluted with water (200 mL), then extracted with methyl tert-butyl ether (300 mL×5). The combined organic phases were dried over anhydrous sodium sulfate, filtered and concentrated under reduced pressure to give N-nitro-L-proline (57.00 g, crude).

Step B: N-nitro-L-proline (57.00 g, crude) was dissolved in toluene (90 mL), cooled to 0° C., and trifluoroacetic anhydride (82.51 mL, 593.21 mmol) was added dropwise within 1 h. The reaction mixture was stirred at 25° C. for 2 h. Potassium carbonate (87.45 g, 632.76 mmol) was dispersed in water (50 mL) and dichloromethane (100 mL), and the previous reaction solution was added dropwise to the solution at 0° C. within 1 h. After the addition was completed, the mixture was stirred at 25° C. for 1 h. The mixture was extracted with dichloromethane (100 mL×5). The combined organic phases were washed with brine (200 mL), dried over anhydrous sodium sulfate, filtered and concentrated under reduced pressure. The residue was purified by silica gel chromatograph (eluent: petroleum ether/ethyl acetate=0/1) to give 5,6-dihydro-4H-pyrrolo[1,2-c][1,2,3]oxadiazol-7-ium-3-olate (39.00 g, yield: 78.20%).

Step C: under nitrogen, 5,6-dihydro-4H-pyrrolo[1,2-c][1,2,3]oxadiazol-7-ium-3-olate (23.5 g, 186.35 mmol) was dissolved in toluene (120 mL), then 2-chloroacetylene tri-n-butyltin (84.67 g, 242.26 mmol) was added. The reaction mixture was stirred at 150° C. for 40 h and directly purified by silica gel chromatograph (eluent: petroleum ether/ethyl acetate=1/0-20/1) to give 2-(tributylstannyl)-5,6-dihydro-4H-pyrrolo[1,2-b]pyrazole (13.00 g, yield: 17.56%).

Preparation of Embodiment 11

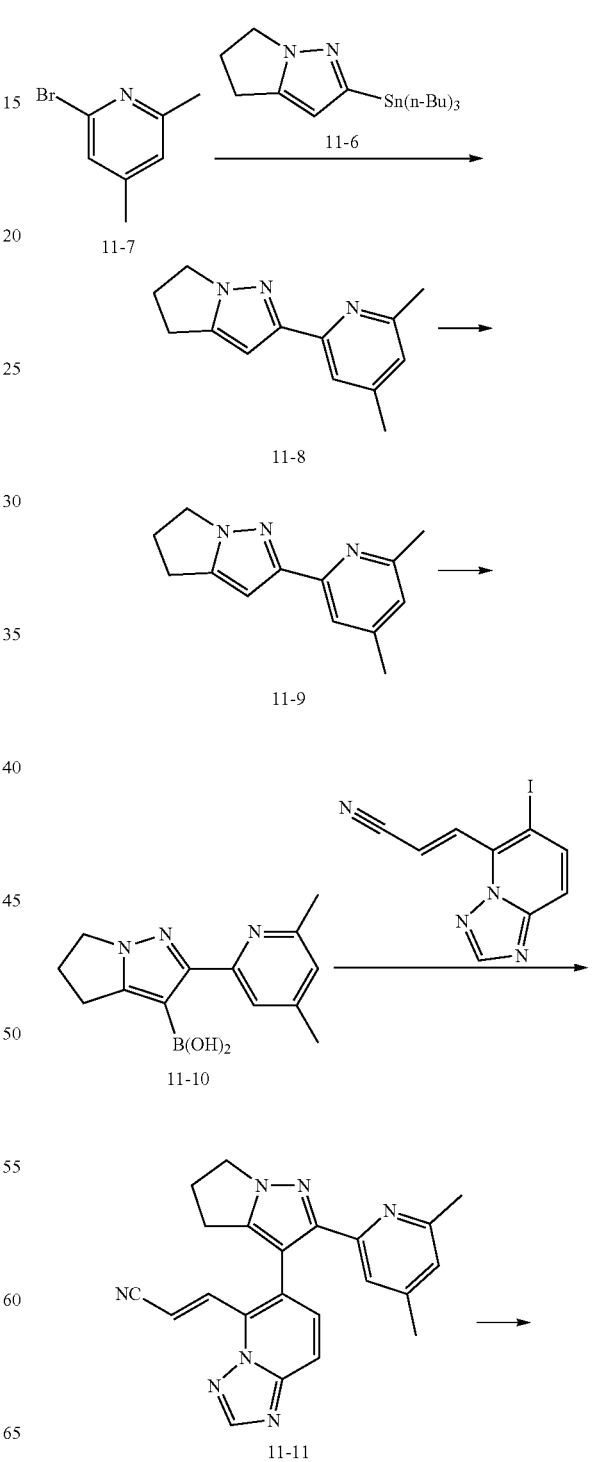

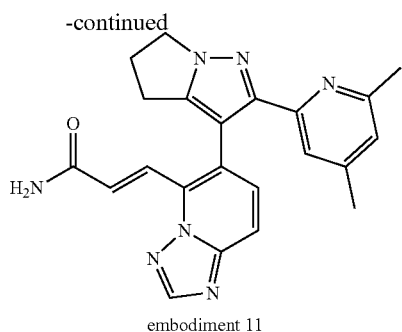

embodiment 11

Step A: 2-(tributylstannyl)-5,6-dihydro-4H-pyrrolo[1,2-b]pyrazole (1.49 g, 3.76 mmol), 2-bromo-4,6-dimethylpyridine (700.00 mg, 3.76 mmol), lithium chloride (318.98 mg, 7.52 mmol) and tetrakis(triphenylphosphine)palladium (434.77 mg, 376.24 μmol) were added to dioxane (20 mL). The reaction mixture was charged with nitrogen three times, then heated to 100-110° C. and stirred for 12 h. LCMS monitoring showed that 2-(tributylstannyl)-5,6-dihydro-4H-pyrrolo[1,2-b]pyrazole was not consumed completely. The reaction was stirred for another 12 h at 100-110° C. Again LCMS monitoring showed that 2-(tributylstannyl)-5,6-dihydro-4H-pyrrolo[1,2-b]pyrazole was not consumed completely. The reaction was further stirred for 12 h at 100-110° C. Finally, the reaction monitored by LCMS was completed. Then the reaction mixture was quenched by pouring into water (50 mL) and extracted with ethyl acetate (50 mL×3). The combined organic phases were washed with brine (100 mL), dried over anhydrous sodium sulfate, filtered and concentrated under reduced pressure. The residue was purified by preparative silica gel chromatography (eluent: dichloromethane/methanol=30/1) to give 2-(4,6-dimethylpyridin-2-yl)-5,6-dihydro-4H-pyrrolo[1,2-b]pyrazole (649.00 mg, yield: 63.81%, purity: 78.847%).

Step B: 2-(4,6-dimethylpyridin-2-yl)-5,6-dihydro-4H-pyrrolo[1,2-b]pyrazole (150.00 mg, 703.30 μmol) and NBS (137.69 mg, 773.63 μmol) were dissolved in N,N-dimethylformamide (3 mL). The reaction mixture was stirred at 15-20° C. for 2 h, then quenched by pouring into water (15 mL) and extracted with ethyl acetate (20 mL×3). The combined organic phases were washed with brine (15 mL), dried with anhydrous sodium sulfate, filtered and concentrated under reduced pressure. The residue was purified by preparative silica gel chromatography (eluent: dichloromethane/methanol=30/1) to give 3-bromo-2-(4,6-dimethylpyridin-2-yl)-5,6-dihydro-4H-pyrrolo[1,2-b]pyrazole (150.00 mg, yield: 73.00%).

Step C: 3-bromo-2-(4,6-dimethylpyridin-2-yl)-5,6-dihydro-4H-pyrrolo[1,2-b]pyrazole (150.00 mg, 513.40 μmol) and triisopropyl borate (255.87 mg, 1.36 mmol, 312.04 μL) were dissolved in tetrahydrofuran (4 mL). The mixture was cooled to −78−−60° C., then n-butyllithium (2.5 M, 533.94 μL) was added dropwise. The reaction mixture was warmed to 15-20° C. and stirred for 30 min, then quenched by pouring to saturated ammonium chloride solution (20 mL) and extracted with ethyl acetate (20 mL×2). The combined organic phases were washed with brine (30 mL), dried over anhydrous sodium sulfate, filtered and concentrated under reduced pressure. The residue was purified by preparative silica gel chromatography (eluent: dichloromethane/methanol=30/1) to give (2-(4,6-dimethylpyridin-2-yl)-5,6-dihydro-4H-pyrrolo[1,2-b]pyrazol-3-yl)boronic acid (90.00 mg, yield: 68.18%).

Step D: (E)-3-(6-iodo-[1,2,4]triazolo[1,5-a]pyridin-5-yl)acrylonitrile (100.00 mg, 337.76 μmol), (2-(4,6-dimethylpyridin-2-yl)-5,6-dihydro-4H-pyrrolo[1,2-b]pyrazol-3-yl)boronic acid (86.84 mg, 337.76 μmol), sodium carbonate (107.40 mg, 1.01 mmol), [1,1'-bis(diphenylphosphino)ferrocene]palladium dichloride (7.41 mg, 10.13 μmol), dicyclohexylphosphine-2'6'-dimethoxybiphenyl (1.39 mg, 3.38 μmol) and [2-(2-aminophenyl)phenyl]-chloro-palladium; cyclohexyl-[2-(2,6-dimethoxyphenyl)phenyl]phosphine (12.17 mg, 16.89 μmol) were added to a mixed solvent of dioxane (20 mL) and water (4 mL). The reaction mixture was charged with nitrogen three times, then heated to 80-90° C. and stirred for 12 h. Then the mixture was quenched by pouring into water (30 mL) and extracted with ethyl acetate (30 mL×2). The combined organic phases were washed with brine (40 mL), dried over anhydrous sodium sulfate, filtered and concentrated under reduced pressure. The residue was purified by preparative silica gel chromatography (eluent: dichloromethane/methanol=30/1) to afford (E)-3-(6-(2-(4,6-dimethylpyridin-2-yl)-5,6-dihydro-4H-pyrrolo[1,2-b]pyrazol-3-yl)-[1,2,4]triazolo[1,5-a]pyridin-5-yl)acrylonitrile (80.00 mg, crude).

Step E: (E)-3-(6-(2-(4,6-dimethylpyridin-2-yl)-5,6-dihydro-4H-pyrrolo[1,2-b]pyrazol-3-yl)-[1,2,4]triazolo[1,5-a]pyridin-5-yl)acrylonitrile (80.00 mg, crude) was dissolved in a mixed solvent of water (1 mL) and dimethyl sulfoxide (2 mL), then sodium hydroxide (10.49 mg, 262.18 μmol) and hydrogen peroxide (74.31 mg, 655.45 μmol) were added in one portion respectively. The reaction mixture was stirred at 15-20° C. for 2 h then quenched by pouring into water (20 mL) and extracted with dichloromethane (20 mL×3). The combined organic phases were washed with brine (50 mL), dried with anhydrous sodium sulfate, filtered and concentrated under reduced pressure. The residue was purified by preparative silica gel chromatography (eluent: dichloromethane/methanol=30/1), and the crude product was impure monitored by LCMS. The crude product was purified again by preparative HPLC (column: Phenomenex Synergi C18 150×30 mm×4 μm; mobile phase: [water (0.225% formic acid)-acetonitrile]; gradient: 10%-40%, 12 min) to give Embodiment 11 (12.00 mg, formate, yield: 22.90%). $^1$H NMR (400 MHz, METHANOL-d4) δ 8.53 (s, 1H), 8.21 (br s, 1H), 8.00 (d, J=15.8 Hz, 1H), 7.76 (d, J=9.2 Hz, 1H), 7.68-7.56 (m, 2H), 7.38 (s, 1H), 6.99 (s, 1H), 4.34 (t, J=6.7 Hz, 2H), 2.97-2.89 (m, 2H), 2.80-2.69 (m, 2H), 2.31 (s, 3H), 2.17 (s, 3H)

Embodiment 12

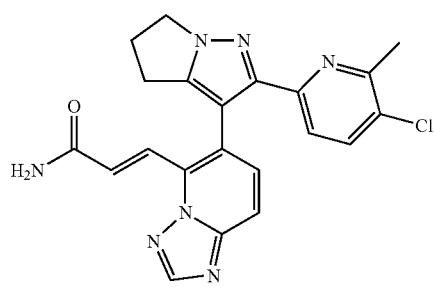 [SMILES: Cc1nc(-c2nn3c(c2-c2ccc4ncnn4c2/C=C/C(N)=O)CCC3)ccc1Cl]

Preparation of Intermediate 12-3

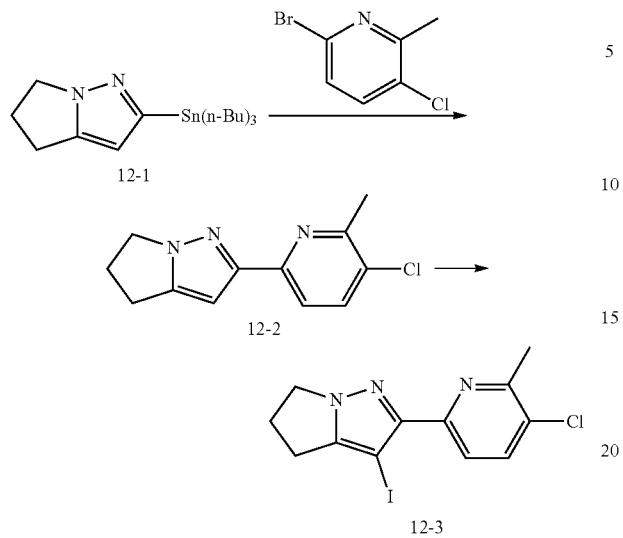

Step A: 2-(tributylstannyl)-5,6-dihydro-4H-pyrrolo[1,2-b]pyrazole (2.69 g, 6.78 mmol), 6-bromo-3-chloro-2-methyl-pyridine (700.00 mg, 3.39 mmol), lithium chloride (287.43 mg, 6.78 mmol) and tetrakis(triphenylphosphine)palladium (391.77 mg, 339.00 μmol) were added to dioxane (30 mL). The reaction mixture was charged with nitrogen three times, then heated to 100-110° C. and stirred for 12 h. The mixture was quenched by pouring into water (50 mL) and extracted with ethyl acetate (50 mL×3). The combined organic phases were washed with brine (100 mL), dried over anhydrous sodium sulfate, filtered and concentrated under reduced pressure. The residue was purified by silica gel chromatograph (eluent: petroleum ether/ethyl acetate=10/1-5/1) to give 2-(5-chloro-6-methylpyridin-2-yl)-5,6-dihydro-4H-pyrrolo[1,2-b]pyrazole (600.00 mg, yield: 67.19%). $^1$H NMR (400 MHz, CHLOROFORM-d) 7.65 (q, J=8.4 Hz, 2H), 6.59 (s, 1H), 4.22 (t, J=7.2 Hz, 2H), 2.95 (t, J=7.3 Hz, 2H), 2.71-2.59 (m, 5H).

Step B: 2-(5-chloro-6-methylpyridin-2-yl)-5,6-dihydro-4H-pyrrolo[1,2-b]pyrazole (200.00 mg, 855.80 μmol) was dissolved in N,N-dimethylformamide (3 mL) and then NIS (211.79 mg, 941.38 μmol) was added in one portion. The reaction mixture was stirred at 15-20° C. for 12 h, then filtered, and the filter cake was collected, concentrated and dried to give 2-(5-chloro-6-methylpyridin-2-yl)-3-iodo-5,6-dihydro-4H-pyrrolo[1,2-b]pyrazole (264.00 mg, yield: 85.79%).

Preparation of Embodiment 12

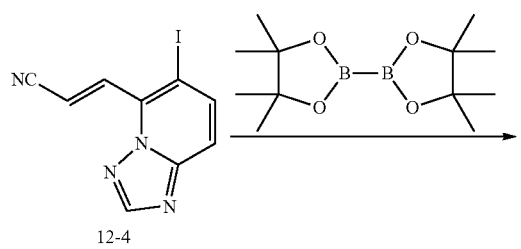

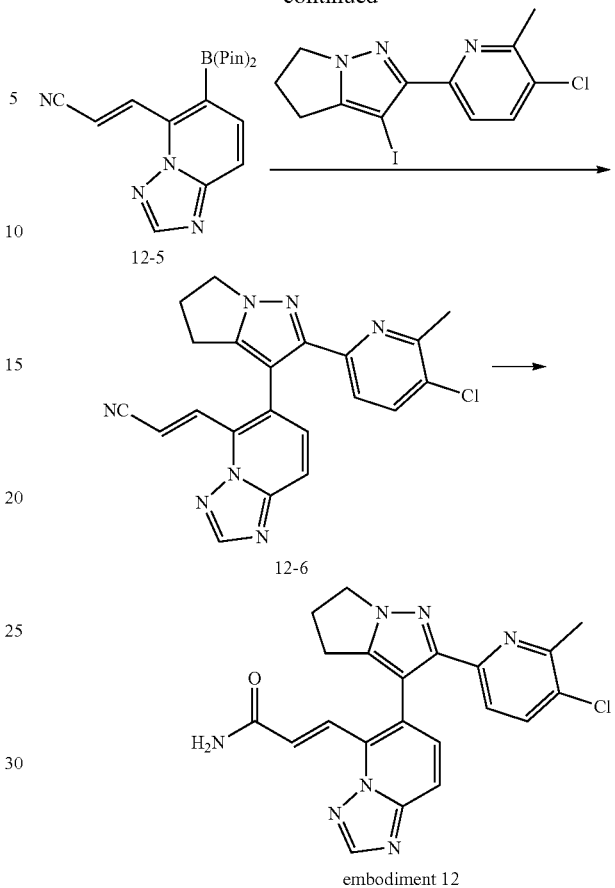

embodiment 12

Step A: (E)-3-(6-iodo-[1,2,4]triazolo[1,5-a]pyridin-5-yl)acrylonitrile (200.00 mg, 675.52 μmol), bis(pinacolato)diboron (205.85 mg, 810.62 μmol), [1,1'-bis(diphenylphosphino)ferrocene]palladium dichloride (49.43 mg, 67.55 μmol) and potassium acetate (132.59 mg, 1.35 mmol) were added to dioxane (20 mL). The reaction mixture was charged with nitrogen three times, then heated to 100-110° C. and stirred for 12 h. The reaction was left untreated and the solution was used directly in the next step.

Step B: 2-(5-chloro-6-methylpyridin-2-yl)-3-iodo-5,6-dihydro-4H-pyrrolo[1,2-b]pyrazole (121.43 mg, 337.69 μmol), sodium carbonate (107.38 mg, 1.01 μmol), [1,1'-bis(diphenylphosphino)ferrocene]palladium dichloride (24.71 mg, 33.77 μmol), dicyclohexylphosphine-2'6'-dimethoxybiphenyl (13.86 mg, 33.77 μmol), [2-(2-aminophenyl)phenyl]chloro-palladium; cyclohexyl-[2-(2,6-dimethoxyphenyl)phenyl]phosphine (24.33 mg, 33.77 μmol), dioxane (4.00 mL) and water (4.00 mL) were added to the mixture in step A. The reaction mixture was charged with nitrogen three times, then heated to 90-100° C. and stirred for 2 h. The mixture was quenched by pouring into water (30 mL) and extracted with ethyl acetate (30 mL×2). The combined organic phases were washed with brine (50 mL), dried over anhydrous sodium sulfate, filtered and concentrated under reduced pressure. The residue was purified by preparative silica gel chromatography (eluent: dichloromethane/methanol30/1) to afford (E)-3-(6-(2-(5-chloro-6-methylpyridin-2-yl)-5,6-dihydro-4H-pyrrolo[1,2-b]pyrazol-3-yl)-[1,2,4]triazolo[1,5-a]pyridin-5-yl)acrylonitrile (120.00 mg, yield: 88.43%).

Step C: (E)-3-(6-(2-(5-chloro-6-methylpyridin-2-yl)-5,6-dihydro-4H-pyrrolo[1,2-b]pyrazol-3-yl)-[1,2,4]triazolo[1,5-a]pyridin-5-yl)acrylonitrile (120.00 mg, 298.62 μmol) was dissolved in a mixed solvent of dimethyl sulfoxide (2 mL) and water (1 mL), then hydrogen peroxide (338.54 mg, 2.99 mmol) and sodium hydroxide (2 mol/L, 597.24 μL) were added in sequence. The reaction mixture was stirred at 15-20° C. for 12 h. The LCMS monitoring showed the reaction was not completed. Then the reaction mixture was heated to 40-50° C. and stirred for 2 h. LCMS monitoring indicated completion of the reaction. The mixture was quenched by pouring into water (10 mL) and extracted with dichloromethane (30 mL×2). The combined organic phases were dried over anhydrous sodium sulfate, filtered and concentrated under reduced pressure. The residue was purified by preparative high performance liquid chromatography (column: Phenomenex Synergi C18 150×30 mm×4 μm; mobile phase: [water (0.225% formic acid)-ACN]; gradient: 24%-54%, 12 min) to give embodiment 12 (21.46 mg, yield: 15.72%). $^1$H NMR (400 MHz, METHANOL-d4) δ 8.56 (s, 1H), 8.06 (d, J=15.6 Hz, 1H), 7.79 (d, J=9.0 Hz, 1H), 7.73-7.61 (m, 4H), 4.34 (br d, J=6.0 Hz, 2H), 2.94-2.85 (m, 2H), 2.73 (br s, 2H), 2.17 (s, 3H).

Experiment 1: Test of Inhibitory Activity of TGFβ-RI In Vitro

Experimental Method i) Test compound: the $IC_{50}$ was determined by diluting into 10 gradient points with each gradient by three-fold dilution and with a starting concentration of 5 μM.

ii) The $IC_{50}$ of reference compound LDN193189 was determined by diluting into 10 gradient points with each gradient by three-fold dilution and with a starting concentration of 20 μM.

iii) The reaction system contains 10 μM ATP.

iv) Calculate the $IC_{50}$ value by curve fitting when the percentage of enzyme activity (compared to the solvent group) is below 65% at the highest concentration of the sample.

Experimental Results: See Table 1

Conclusion: the compound of the present invention has excellent inhibitory activity in vitro.

TABLE 1

| Sample | TGF-βRI $IC_{50}$ |
|---|---|
| Embodiment 1 | A |
| Embodiment 2 | B |
| Embodiment 3 | B |
| Embodiment 4 | B |
| Embodiment 5 | B |
| Embodiment 6 | B |
| Embodiment 7 | B |
| Embodiment 8 | B |
| Embodiment 9 | B |
| Embodiment 10 | B |
| Embodiment 11 | C |
| Embodiment 12 | C |

[Note]
The range of $IC_{50}$ values is shown as follows: 50 nM ≥ A ≥ 1 nM; 500 nM ≥ B > 50 nM; C > 500 nM.

Experiment 2: Test of Proliferation Inhibition on NIH/3T3 Mouse Embryonic Cells

Experimental Principle:

Promega's Luminescent Cell Viability Assay (CellTiter-Glo® method, i.e. ATP fluorescence activity detection and analysis), the compound is added to the cell culture plate for incubation. A substrate buffer for detecting intracellular ATP content was added on the day of detection. Slightly shake and centrifuge at 1000 rpm for 1 min. Tested after standing for 10 min. The assay plate was analyzed using Envision multifunctional enzyme marker of PerkinElmer, Inc., and the analysis mode was fluorescence detection, and the data was expressed by the reading of chemiluminescence signal at 400-700 nm.

Experimental Steps i) When the cell growth coverage is about 70%, the cell layer was washed with 10 mL of Duchenne phosphate buffer (D-PBS) which is calcium- and magnesium-free, then 2 mL of 0.25% trypsin-EDTA digest was added. The cell culture flask was placed in a $CO_2$ carbon dioxide incubator at 37° C. and incubated for 3-5 min, then 8 mL of complete culture medium containing 2% FBS DMEM cells was added, and the cells were puffed evenly into single cell and counted by Vi-cell cytometer, and NIH/3T3 cell suspension was diluted to $0.375 \times 10^5$/mL cells.

ii) 50 μL of 2% DMEM-containing medium was added around the 384-well cell culture plate, then 40 μL of cell suspension was added to the remaining wells to 1500 cells per well. The distribution of the cells was observed under a microscope, and the cell plates were placed in a cell culture incubator with 5% $CO_2$ at 37° C.

iii) Dilution of the compound refers to the preparation of the compound.

iv) A mixture of 2% fetal bovine serum containing 1 ng/mL TGF-β1 in DMEM medium was added manually to the compound intermediate plate, 20 μL per well.

v) The compound intermediate plate was shook slightly for 10 sec at 1000 rpm/min and centrifuge for 10 sec.

vi) 10 uL of the mixed liquid from steps 4 and 5 of each well was transferred to the inoculated cell plate to a final volume of 50 μL by using a Bravo liquid workstation, and the final concentration of TGF-β1 was diluted to 0.2 ng/mL, and centrifuged for 10 sec at 1000 rpm/min. The plates were placed in an incubator with 5% carbon dioxide at 37° C., 5% carbon dioxide for 72 h. The final concentration of the compound is: (unit: μM)

| 30 | 9.488 | 3.001 | 0.949 | 0.300 | 0.095 | 0.030 | 0.009 | 0.003 | vii) The cell plate containing the compound was cultured in a cell incubator with 5% $CO_2$ at 37° C. for 3 days.

viii) After that, 25 μL of ATP fluorescence activity detection solution was added to each well of the cell plate, then shook gently for about 1 min and centrifuged at 500 rpm/min for about 30 sec, and the reading was performed in an Envision instrument after standing at room temperature for 10 min in the dark.

Experimental Results: See Table 2

TABLE 2

| Sample | Proliferation inhibition on NIH3T3 $IC_{50}$ |
| --- | --- |
| Embodiment 1 | A |
| Embodiment 2 | B |
| Embodiment 3 | B |
| Embodiment 4 | B |
| Embodiment 5 | C |
| Embodiment 6 | A |
| Embodiment 8 | B |
| Embodiment 9 | A |
| Embodiment 10 | B |

[Note]
The range of $IC_{50}$ values is shown as follows: 2 μM ≥ A ≥ 0.5 μM; 5 μM ≥ B > 2 μM; C > 5 μM.

Conclusion: the compound of the present invention has excellent NIH3T3 cell proliferation inhibitory activity.

Experiment 3: Tumor Cell Proliferation Inhibition Experiment in a BALB/c Mouse Model of Tumor of Mouse Rectal Cancer CT-26 Cells Subcutaneously Transplanted in Combination with BioXcell-mPD-L1

Experiment Design:
The following table lists the animal grouping and dosing regimen of embodiment 1, the positive reference compound LY2157299 and the BioXcell PD-L1 monoclonal antibody (BioXcell-mPD-L1), which are used alone or in combination in vivo. See table 3.

TABLE 3

Animal grouping and dosing regimen

| Group | Number of mice | Compound therapy | Dose (mg/kg) | Dosing volume parameter (μl/g) | Route of administration | Frequency of administration |
| --- | --- | --- | --- | --- | --- | --- |
| 1 | 12 | Solvent control | — | 10 | PO | Twice a day × 3 weeks |
| 2 | 12 | Embodiment 1 | 75 | 10 | PO | Twice a day × 3 weeks |
| 3 | 12 | LY2157299 | 75 | 10 | PO | Twice a day × 3 weeks |
| 4 | 12 | BioXcell-mPD-L1 | 10 | 10 | IP | Twice a week × 3 weeks |
| 5 | 12 | Embodiment 1 + BioXcell-mPD-L1 | 75 + 10 | 10 | PO + IP | Twice a day × 3 weeks + twice a week × 3 weeks |
| 6 | 12 | LY2157299 + BioXcell-mPD-L1 | 75 + 10 | 10 | PO + IP | Twice a day × 3 weeks + twice a week × 3 weeks |

Experimental Methods and Steps:
i) Cell Culture
Mouse colon cancer CT-26 cells were cultured in vitro in a single layer, and culture conditions is RPMI1640 medium (Medium No. 1640, Roswell Parker Memorial Institute) supplemented with 10% fetal bovine serum at 37° C., 5% $CO_2$. Passage was routinely digested with trypsin-EDTA twice a week. When the cell saturation is 80%-90%, the cells are collected, counted, and inoculated.

ii) Tumor Cell Inoculation
0.1 mL ($1 \times 10^5$) CT-26 cells were subcutaneously inoculated into the right back of each BALB/c mouse. The mice were administered in groups according to the body weight of the mice on the second day after cell inoculation.

iii) Tumor Measurement and Experimental Indicators
The experimental indicator is to investigate whether tumor growth is inhibited, delayed or cured. Tumor diameters were measured with Vernier calipers twice a week. The tumor volume is calculated as: $V=0.5a \times b^2$, and a and b represent the long and short diameters of the tumor, respectively.

The antitumor effect of the compound was evaluated by TGI (%) or tumor proliferation rate T/C (%). TGI (%) reflects the tumor growth inhibition rate. Calculation of TGI (%): TGI (%)=[(1-(mean tumor volume at the end of administration of a treatment group—mean tumor volume at the start of administration of the treatment group))/(mean tumor volume at the end of treatment of the solvent control group)—mean tumor volume at the start of treatment of the solvent control group)]×100%.

Tumor proliferation rate T/C (%): The formula is as follows: T/C %=T/C×100% (T: treatment group; C: negative control group).

Tumor weights were measured after the end of the experiment and the percentage of $T/C_{weight}$ was calculated. $T_{weight}$ and $C_{weight}$ represent the tumor weights of the drug-administered group and the vehicle control group, respectively.

vi) PK Sample Collection
On the 20th day after administration, administration was carried out according to the dosing regimen.

Twelve mice were divided into 4 groups, and blood was collected at 0.25, 1, 1.5, 4, and 8 h after the last administration; the mice were sacrificed at 0.25, 1, 4, and 8 h to collect tumors and liver. Whole blood was placed in a 0.5 mL EDTA-2K anticoagulant tube, centrifuged at 7000 rpm, 4° C. for 10 min to obtain plasma. Tumor tissue was placed in a 10 mL cryotube. Plasma and tumor tissues were quickly transferred to a −80° C. freezer for storage.

v) Statistical Analysis
Statistical analysis, including mean and standard error (SEM) of tumor volume at each time point for each group (see Table 4 for specific data). The treatment group showed the best therapeutic effect on the 20th day after the administration at the end of the trial, and therefore statistical analysis was performed based on this data to evaluate the difference between the groups. T-test was used for comparison between the two groups, and one-way analysis of variance was used for comparison between three or more groups. If there was a significant difference in F values, the Gass-Howell method was used to test. If there is no significant difference in F values, the Dunnet (2-sided) method is used for analysis. All data analysis was performed with SPSS 17.0. A significant difference was considered at $p<0.05$.

Experimental Results:

i) Mortality, Morbidity and Weight Changes

The body weight of experimental animals was used as a reference indicator for indirect determination of drug toxicity. None of the drug-administered groups in this model showed significant weight loss, no morbidity or death.

Effects of embodiment 1, LY2157299 and BioXcell-mPD-L1 on the body weight of CT-26 cells subcutaneous xenograft tumor female BALB/c mouse model are shown in FIG. 1. Data points represent the average body weight within the group and error bars represent standard errors (SEM).

ii) Tumor Volume

The tumor volume changes of female BALB/c mice of CT-26 cells subcutaneously transplanted after embodiment 1, LY2157299 and BioXcell-mPD-L1 treatment are shown in Table 4.

iii) Tumor Growth Curve

Figure 2:
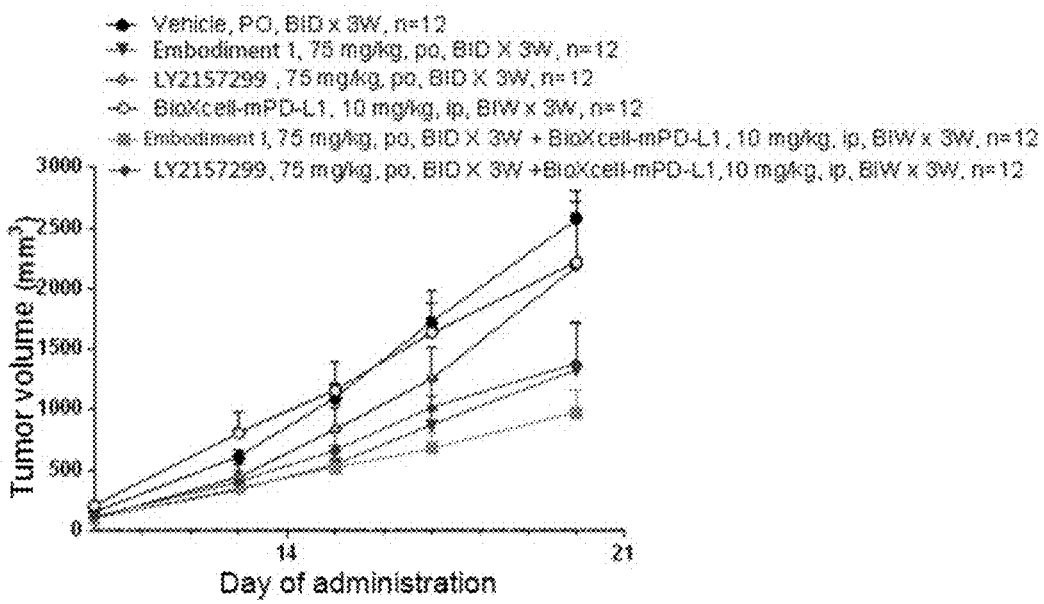
FIG. 2 is a tumor growth curve of CT-26 xenograft model tumor-bearing mice after administration of Embodiment 1, LY2157299 and BioXcell-mPD-L1.

Tumor growth curves of CT-26 xenograft model tumor-bearing mice after administration of embodiment 1, LY2157299 and BioXcell-mPD-L1 are shown in FIG. 2. Data points represent the mean tumor volume within the group and error bars represent standard errors (SEM).

1331, 2186, 2218 and 1381 mm³ respectively (T/C=51%, 85%, 86% and 54%, p=0.071, 0.906, 0.932 and 0.089).

Experiment 4: Tumor Cell Metastasis Inhibition Experiment in BALB/c Mouse Orthotopic Transplantation Model of Mouse Breast Cancer 4T1 Cells Experimental Method:

i) Establishment of an In Situ 4T1 Tumor Model:

Fluorescently labeled mouse breast cancer 4T1-Luc cells were expanded in vitro. Before the cells were collected, the mice were anesthetized with intraperitoneal injection of sodium pentobarbital. After anesthetized mice were fixed, the abdominal skin was disinfected with 70% alcohol. 100 uL of phosphate buffer (containing $0.5\times10^6$ 4T1-luc2 cells) was inoculated into the left side of the fourth pair of abdominal mammary fat pads in mice, and the incision was sutured to disinfect the skin. The animals are kept warm with a warm blanket, observed until they wake up and put back in their cages. 0.1 mg/kg buprenorphine for pain relief was subcutaneously injected 30 min before surgery and 6 hours after surgery.

ii) Group Treatment Plan:

On the third day after modeling, the animals were subjected to bioluminescence detection by infrared data imaging, randomly grouped according to the fluorescence values, and administered according to the following experimental protocol, see Table 5.

iii) Experimental Endpoint Design:

To observe the inhibitory effect of embodiment 1 on tumor growth and metastasis, the experimental endpoint was designed to be 30-35 days after administration, with reference to historical data of the model. At the end of the

TABLE 4

Tumor volume at different time points in each group

| | | | Tumor volume (mm³)[a] | | | |
|---|---|---|---|---|---|---|
| Day of administration | Solvent control | Embodiment 1 75 mg/kg | LY2157299 75 mg/kg | BioXcell-mPD-L1 10 mg/kg | Embodiment 1 + BioXcell-mPD-L1 75 mg/kg + 10 mg/kg | LY2157299 + BioXcell-mPD-L1 75 mg/kg + 10 mg/kg |
| 10 | 156 ± 20 | 102 ± 19 | 98 ± 14 | 205 ± 24 | 99 ± 12 | 120 ± 16 |
| 13 | 608 ± 62 | 339 ± 89 | 446 ± 104 | 808 ± 169 | 357 ± 72 | 404 ± 94 |
| 15 | 1091 ± 120 | 552 ± 147 | 840 ± 177 | 1160 ± 243 | 517 ± 118 | 661 ± 147 |
| 17 | 1720 ± 160 | 874 ± 240 | 1256 ± 257 | 1636 ± 343 | 680 ± 136 | 1012 ± 238 |
| 20 | 2578 ± 229 | 1331 ± 394 | 2186 ± 435 | 2218 ± 502 | 975 ± 193 | 1381 ± 327 |

[Note]:
[a]Average ± SEM.

Conclusion:

This experiment evaluated the in vivo efficacy of embodiment 1, positive control LY2157299 and BioXcell-mPD-L1 in a murine colon cancer CT-26 xenograft model. Twenty days after the start of administration, the tumor volume of the tumor-bearing mice in the solvent control group reached 2578 mm³. The combination of embodiment 1 (75 mg/kg) and BioXcell-mPD-L1 (10 mg/kg) had a significant antitumor effect compared with the solvent control group (T/C=38%, TGI=62.2%, p=0.012), tumor volume was 975 mm³; embodiment 1 (75 mg/kg), LY2157299 (75 mg/kg), BioXcell-mPD-L1 (10 mg/kg) alone, and the combined doses of LY2157299 (75 mg/kg) and BioXcell-mPD-L1 (10 mg/kg) showed no significant antitumor effect compared with the solvent control group. The tumor volumes were experiment, the in situ tumor and various organ tissues were dissected, the tumor was weighed, and the fluorescence intensity of each organ was detected by IVIS fluorescence. Growth inhibition of orthotopic tumors can be compared by the weight of the in situ tumor in the experimental endpoint, and the inhibition curve is generated from the tumor volume measurement data twice a week during the experiment. The inhibition of tumor metastasis was determined by the presence or absence of fluorescence detection of each organ and the analysis of relative fluorescence intensity.

At the end of the experiment, the tumor weight will be detected and the relative tumor growth rate T/C (%) will be calculated; the tumor volume is calculated as: $V=0.5a\times b^2$, and a and b represent the long and short diameters of the tumor, respectively. At the same time, the lung, liver, spleen, kidney, intestine and left upper limb were stripped, and fluorescence was detected to determine whether there was metastasis and metastasis intensity and ratio.

The antitumor effect of the compound was evaluated by the tumor growth inhibition rate TGI (%) or the relative tumor growth rate T/C (%).

Calculation of TGI (%):

TGI (%)=[(1−mean tumor volume at the end of administration of a treatment group−mean tumor volume at the start of administration of the treatment group))/(mean tumor volume at the end of treatment of the solvent control group−mean tumor volume at the start of administration of the solvent control group)]×100%.

Relative tumor growth rate T/C (%) calculation:

T/C(%)=Tt(treatment group)/Ct(control group)×100%,

Tt is the average tumor volume at a certain measurement, and Ct takes the same day data.

The experimental results were statistically analyzed using one-way ANOVA. If there is a significant difference in F values, multiple comparisons should be made after ANOVA analysis. All data in this experiment were analyzed using SPSS 17.0. A significant difference was considered at $p<0.05$.

TABLE 5

Animal grouping and dosing regimen

| Group | Number of mice | Compound therapy | Dose (mg/kg) | Dosing volume parameter (μl/g) | Route of administration | Frequency of administration |
|---|---|---|---|---|---|---|
| 1 | 12 | Solvent control | — | 10 | PO | Once a day × 32 |
| 2 | 12 | LY2157299 | 75 | 10 | PO | Once a day × 32 |
| 3 | 12 | Embodiment 1 | 75 | 10 | PO | Once a day × 32 |

Experimental Results:

i) Changes in Animal Body Weight

Figure 3:
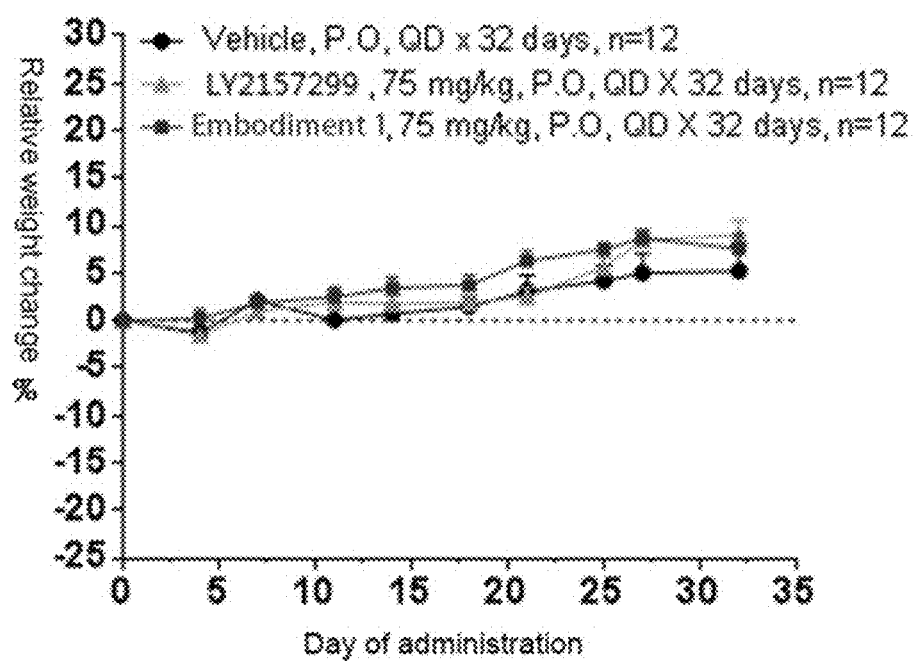
FIG. 3 is the relative weight changes of animals in the tumor cell metastasis inhibition test of BALB/c mouse orthotopic transplantation model of mouse breast cancer 4T1 cells.

Relative body weight changes were calculated based on animal body weight at the start of dosing, as shown in FIG. 3. Data points represent the percentage change in average body weight within the group, and error bars represent standard errors (SEM).

ii) The Inhibitory Effect of Embodiment 1 on the Incidence of Tumor Metastasis

At the end of the experiment, each organ tissue was peeled off, and fluorescence imaging and fluorescence intensity value recording were measured by IVIS for 40 sec exposure within 8 min. The fluorescence imaging results of the tested tissues of the 10 animals excised by the maximum and minimum values are shown in Table 6.

TABLE 6

Effect of treatment of embodiment 1 on the incidence of 4T1 tumor metastasis

| Metastasis rate (%)[a] | Solvent control | LY2245035 | Embodiment 1 |
|---|---|---|---|
| Lung | 100 | 100 | 100 |
| Liver | 90 | 80 | 50 |
| Spleen | 30 | 10 | 0 |
| Kidney | 30 | 30 | 20 |
| Intestine | 80 | 60 | 60 |
| Upper limb | 90 | 70 | 90 |

[Note]:
[a]Number of animals with metastasis in each group/number of animals in the whole group.

iii) Inhibition of Embodiment 1 on Tumor Metastasis Intensity in Each Organ

According to the experimental end point, the fluorescence intensity of each group of organs was normalized by the control group, and the relative fluorescence intensity ratio of each group of organs was obtained. The ratio reflects the level of metastatic intensity on the corresponding organs. The results are shown in Table 7.

TABLE 7

The inhibitory effect of embodiment 1 on the metastatic intensity of various organs

| Metastasis level (%)[a] | Solvent control | LY2245035 | Embodiment 1 |
|---|---|---|---|
| Lung | 100 | 20 | 9 |
| Liver | 100 | 31 | 10 |
| Spleen | 100 | 4 | 0 |
| Kidney | 100 | 121 | 67 |
| Intestine | 100 | 41 | 1 |
| Upper limb | 100 | 54 | 12 |

[Note]:
[a]The average fluorescence value detected by an organ in the drug-administered group/the average fluorescence value detected in an organ of the control group Conclusion:

Comparing the values in the comparison table, embodiment 1 significantly inhibited the metastasis of 4T1 in liver, spleen, kidney and intestine, and the inhibitory effect was significantly better than that of the positive control drug. Embodiment 1 showed significant good inhibition on the occurrence and intensity of metastasis of the tumor in multiple organ tissues and was significantly superior to the positive control drug used in this experiment.

What is claimed is:

1. A compound of formula (I) or a pharmaceutically acceptable salt thereof,

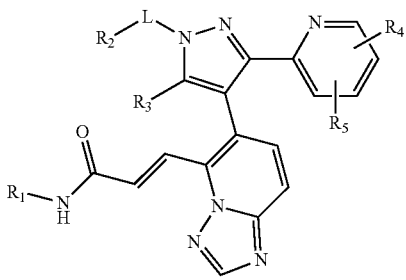 (I)

wherein,
- R₁ is selected from hydrogen, hydroxyl, amino, or from the group consisting of $C_{1-3}$ alkyl, and $C_{3-6}$ cycloalkyl, and the group is optionally substituted by 1, 2, or 3 R(s);
- R₂ is selected from the group consisting of $C_{1-3}$ alkyl, $C_{3-6}$ cycloalkyl and phenyl, and the group is optionally substituted by 1, 2, or 3 R(s);
- R₃ is selected from hydrogen, or from $C_{1-3}$ alkyl which is optionally substituted by 1, 2, or 3 R(s);
- optionally, R₂ and R₃ link together to form a 5-6 membered ring, which is optionally substituted by 1, 2, or 3 R(s);
- each of R₄ and R₅ is independently selected from hydrogen, halogen, or selected from the group consisting of $C_{1-3}$ alkyl and $C_{1-3}$ heteroalkyl, and the group is optionally substituted by 1, 2, or 3 R(s);
- L is selected from a single bond and —(CRR)$_{1-3}$;
- R is selected from F, Cl, Br, I, CN, OH, NH₂, COOH, or from the group consisting of $C_{1-6}$ alkyl, $C_{1-6}$ heteroalkyl, $C_{3-6}$ cycloalkyl, 3-6 membered heterocycloalkyl, phenyl and 5-6 membered heteroaryl, and the group is optionally substituted by 1, 2, or 3 R'(s);
- R' is selected from F, Cl, Br, I, OH, CN, NH₂, COOH, Me, Et, CF₃, CHF₂, CH₂F, NHCH₃, and N(CH₃)₂;
- "hetero" refers to a heteroatom or a heteroatomic group selected from the group consisting of —C(=O)N(R)—, —N(R)—, —C(=NR)—, —S(=O)₂N(R)—, —S(=O)N(R)—, —O—, —S—, =O, =S, —O—N=, —C(=O)O—, —C(=O)—, —C(=S)—, —S(=O)—S(=O)₂—, and —N(R)C(=O)N(R)—;
- in any of the above cases, the number of the heteroatom or the heteroatomic group is independently selected from 1, 2, or 3.

2. The compound or the pharmaceutically acceptable salt thereof according to claim 1, wherein, R is selected from F, Cl, Br, I, CN, OH, or from the group consisting of $C_{1-6}$ alkyl, $C_{3-6}$ cycloalkyl and phenyl, and the group is optionally substituted by 1, 2, or 3 R'(s).

3. The compound or the pharmaceutically acceptable salt thereof according to claim 2, wherein, R is selected from the group consisting of F, Cl, Br, I, CN, OH, methyl, CHF₂, ethyl, propyl, cyclopropyl and phenyl.

4. The compound or the pharmaceutically acceptable salt thereof according to claim 1, wherein, R₁ is selected from hydrogen, or from the group consisting of methyl, ethyl,

and the group is optionally substituted by 1, 2, or 3 R(s).

5. The compound or the pharmaceutically acceptable salt thereof according to claim 4, wherein, R₁ is selected from hydrogen, methyl, ethyl,

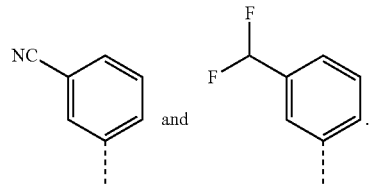

6. The compound or the pharmaceutically acceptable salt thereof according to claim 1, wherein, R₂ is selected from the group consisting of methyl, ethyl, isopropyl, cyclopentyl and phenyl, and the group is optionally substituted by 1, 2, or 3 R(s).

7. The compound or the pharmaceutically acceptable salt thereof according to claim 6, wherein, R₂ is selected from the group consisting of methyl, ethyl, isopropyl, cyclopentyl

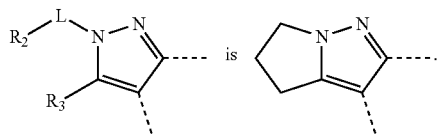

8. The compound or the pharmaceutically acceptable salt thereof according to claim 1, wherein, R₂ and R₃ link together, and the moiety

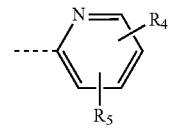

9. The compound or the pharmaceutically acceptable salt thereof according to claim 1, wherein, each of R₄ and R₅ is independently selected from the group consisting of hydrogen, F, Cl, Br, methyl and ethyl.

10. The compound or the pharmaceutically acceptable salt thereof according to claim 1, wherein, the moiety

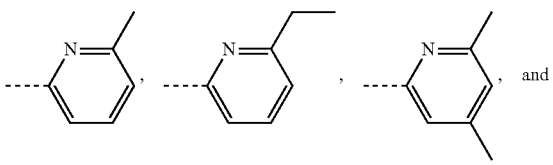

is selected from

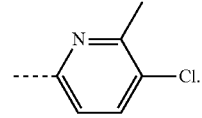

11. The compound or the pharmaceutically acceptable salt thereof according to claim 1, wherein, L is selected from a single bond, —(CH$_2$)$_{1-3}$—.

12. The compound or the pharmaceutically acceptable salt thereof according to claim 11, wherein, L is selected from a single bond, —CH$_2$—, —CH$_2$CH$_2$—.

13. The compound or the pharmaceutically acceptable salt thereof according to claim 1, wherein the compound is selected from

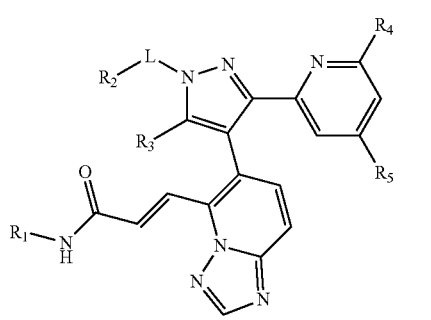
(I-1)

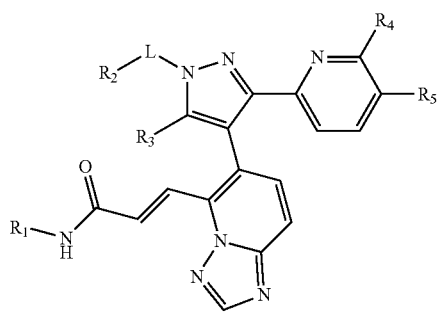
(I-2)

wherein, R$_1$, R$_2$, R$_3$, R$_4$, R$_5$ and L are defined as claim 1, and R$_4$ and R$_5$ are not both hydrogen simultaneously.

14. The compound or the pharmaceutically acceptable salt thereof according to claim 13, wherein the compound is selected from

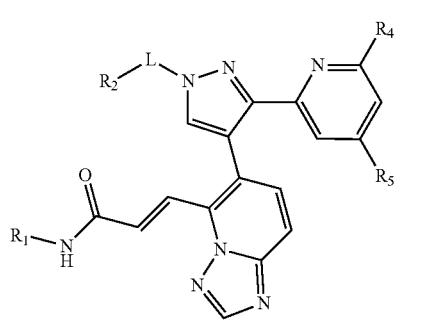
(I-a)

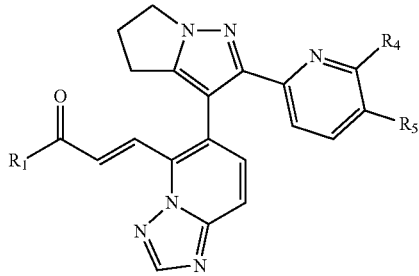
(I-b)

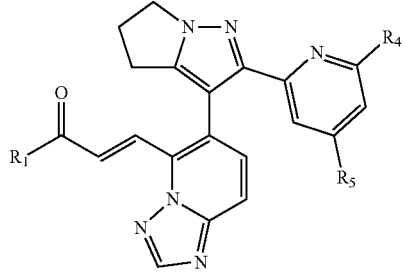
(I-c)

wherein, R$_1$, R$_2$, R$_4$, R$_5$ and L are defined as claim 13, and R$_4$ and R$_5$ are not both hydrogen simultaneously.

15. A compound or a pharmaceutically acceptable salt thereof, which is selected from the group consisting of

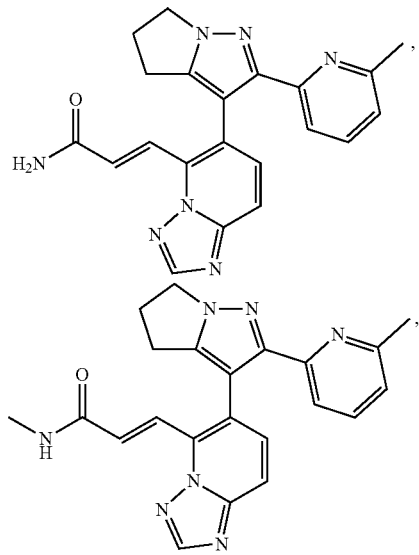

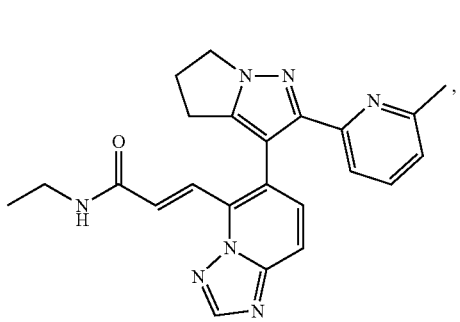

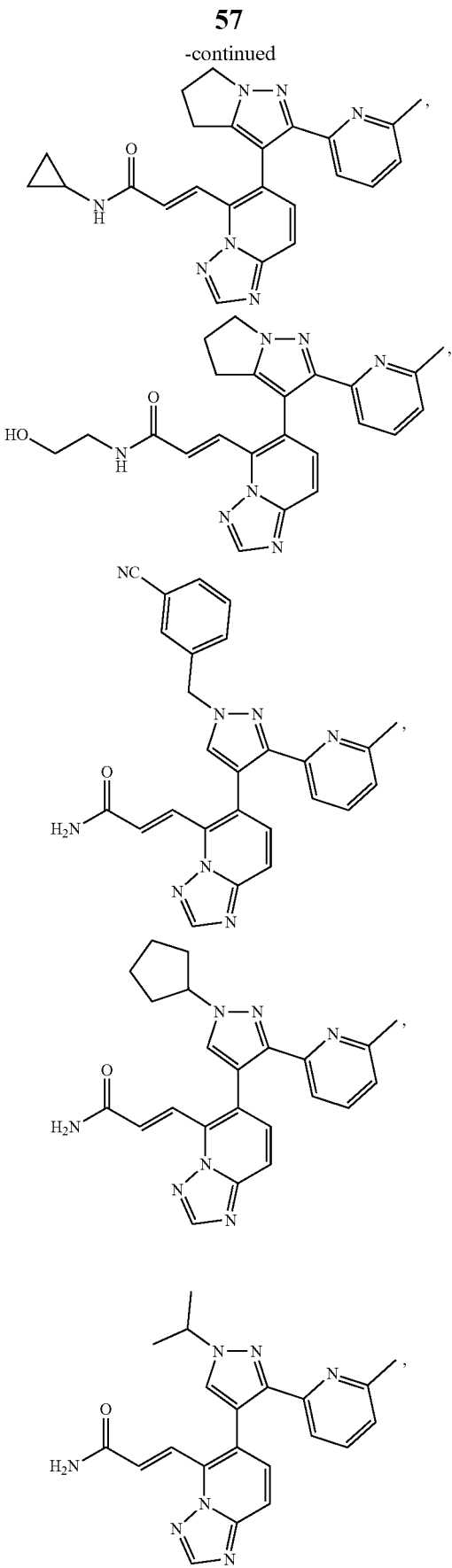

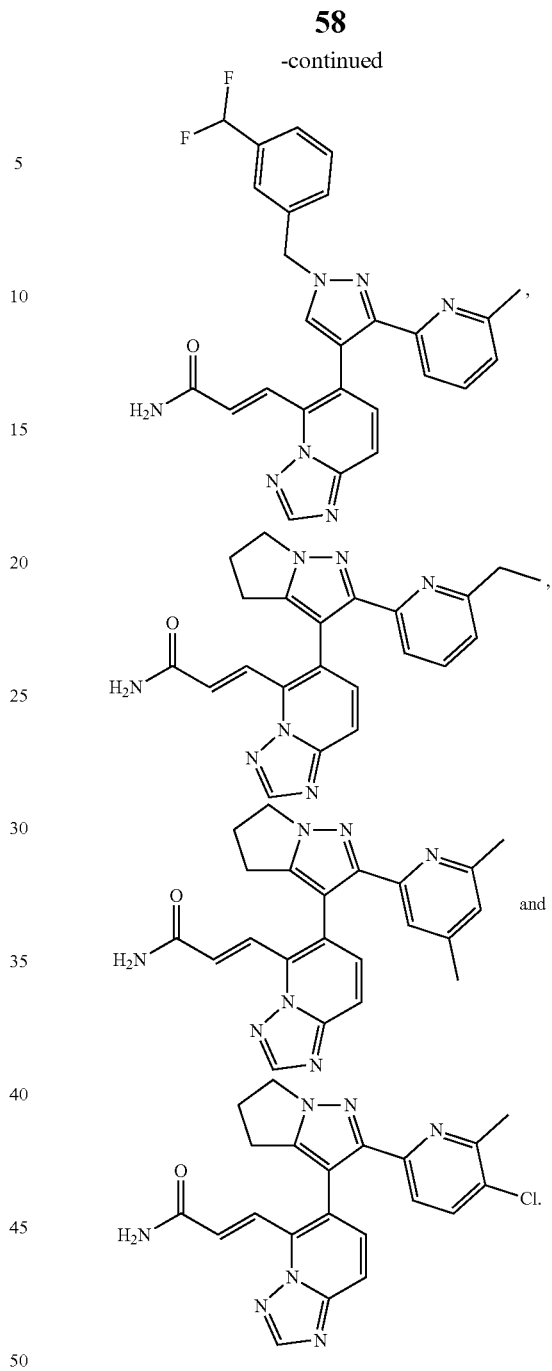

16. A pharmaceutical composition comprising a therapeutically effective dose of the compound or the pharmaceutically acceptable salt thereof according to claim 1 and a pharmaceutically acceptable carrier.

17. A process for treating cancer in a subject in need thereof, comprising: administering an effective amount of the compound or the pharmaceutically acceptable salt thereof according to claim 1 to the subject.

18. A process for treating cancer in a subject in need thereof, comprising: administering an effective amount of the pharmaceutical composition according to claim 16 to the subject.

19. The process according to claim 17, wherein, the cancer is breast cancer.

* * * * *